United States Patent
Morello et al.

(10) Patent No.: US 10,528,884 B2
(45) Date of Patent: Jan. 7, 2020

(54) QUANTUM PROCESSING APPARATUS AND A METHOD OF OPERATING A QUANTUM PROCESSING APPARATUS

(71) Applicant: NewSouth Innovations Pty Limited, Sydney, New South Wales (AU)

(72) Inventors: Andrea Morello, Newtown (AU); Guilherme Tosi, Maroubra (AU); Fahd A. Mohiyaddin, Kensington (AU)

(73) Assignee: NewSouth Innovations Pty Limited, Sydney, New South Wales (AU)

( * ) Notice: Subject to any disclaimer, the term of this patent is extended or adjusted under 35 U.S.C. 154(b) by 0 days.

(21) Appl. No.: 15/565,873

(22) PCT Filed: May 27, 2016

(86) PCT No.: PCT/AU2016/050422
§ 371 (c)(1),
(2) Date: Oct. 11, 2017

(87) PCT Pub. No.: WO2016/187676
PCT Pub. Date: Dec. 1, 2016

(65) Prior Publication Data
US 2018/0107938 A1    Apr. 19, 2018

(30) Foreign Application Priority Data
May 28, 2015   (AU) ............................... 2015901980

(51) Int. Cl.
*G06N 10/00*   (2019.01)
*B82Y 10/00*   (2011.01)
(Continued)

(52) U.S. Cl.
CPC .............. *G06N 10/00* (2019.01); *B82Y 10/00* (2013.01); *G01N 24/10* (2013.01); *G01R 33/60* (2013.01);
(Continued)

(58) Field of Classification Search
CPC ........ B82Y 10/00; G06N 10/00; G01N 24/10; H01L 27/18
See application file for complete search history.

(56) References Cited

U.S. PATENT DOCUMENTS

| | | | |
|---|---|---|---|
| 6,369,404 B1 | 4/2002 | Kane | |
| 6,472,681 B1 | 10/2002 | Kane | |
| 7,547,648 B2 | 6/2009 | Ruess et al. | |
| 2016/0300155 A1* | 10/2016 | Betz | ...................... H01L 39/025 |

FOREIGN PATENT DOCUMENTS

| WO | WO 99/14858 | 3/1999 |
|---|---|---|
| WO | WO 2014/146162 A1 | 9/2014 |

OTHER PUBLICATIONS

Laucht, et al., Electronically controlling single-spin qubits in a continuous microwave field, Condensed Matter Physics, Apr. 10, 2015, pp. 1-5.

(Continued)

*Primary Examiner* — Matthew L Reames
(74) *Attorney, Agent, or Firm* — Knobbe Martens Olson & Bear, LLP

(57) ABSTRACT

The present disclosure provides a method of operation of a quantum processing element and an advanced processing apparatus comprising a plurality of quantum processing elements operated in accordance with the method. Embodiments of the methods disclosed allow using the quantum properties of an MOS structure and a donor atom embedded in the semiconductor to implement electron and nuclear spin qubits and provide multi-qubit coupling, including coupling at longer distances facilitated by a resonator.

17 Claims, 20 Drawing Sheets

(51) Int. Cl.
    *H03K 19/08*     (2006.01)
    *G01N 24/10*     (2006.01)
    *G01R 33/60*     (2006.01)
    *H01L 27/18*     (2006.01)
    *H01L 39/02*     (2006.01)
    *H01L 39/22*     (2006.01)

(52) U.S. Cl.
    CPC ............ *H01L 27/18* (2013.01); *H01L 39/025* (2013.01); *H01L 39/223* (2013.01); *H03K 19/08* (2013.01)

(56) References Cited

OTHER PUBLICATIONS

International Search Report dated Aug. 22, 2016 in corresponding International Application No. PCT/AU2016/050422 filed May 27, 2016.

Loss, DiVincenzo, DP quantum computation with quantum dots. *Phys Rev.* A56, 120; Jan. 1998. (in 7 pages).

Morello, Andrea, et al., Single-Shot readout of an electron spin in silicon. Centre for Quantum Computer Technology, May 24, 2010. (In 5 pages).

Pla, Jarryd J., et al., A single-atom electron spin qubit in silicon. Centre of Excellence for Quantum Computation & Communication Technology, Sep. 19, 2012. (In 13 pages).

Pla., Jarryd J., et al., Hi-findelity readout and control of a nuclear spin qubit in silicon. Centre for Quantum Computer Technology, Apr. 17, 2013. (in 18 pages).

\* cited by examiner

30

32 - Applying a magnetic field to the quantum processing element to separate spin states associated with an electron and a nucleus of the donor atom 34 - Inducing an electric field in the region between the interface and the donor atom to modulate a hyperfine interaction between the electron and the nucleus and control the quantum state of a quantum bit associated with a pair of electron-nuclear spin eigenstates of the electron and the nucleus

FIGURE 3

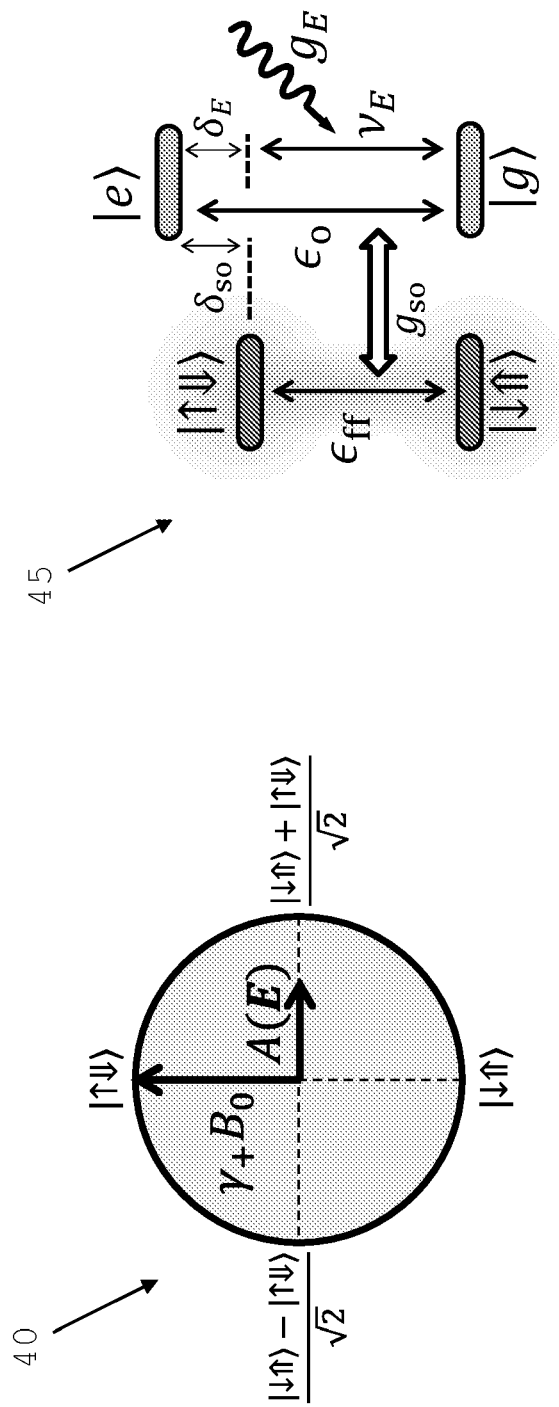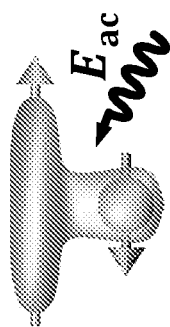
FIGURE 4(c)
FIGURE 4(b)
FIGURE 4(a)

60

62 - Applying a continuous magnetic field to the quantum processing element to separate spin states associated with an electron and a nucleus of the donor atom 64 - Applying an oscillating magnetic field which oscillates at a frequency close to a Zeeman frequency of the electron 66 - Inducing an electric field in the region between the interface and the donor atom to modulate an hyperfine interaction between the electron and the nucleus and control the quantum state of a quantum bit associated with a spin of the nucleus

FIGURE 6

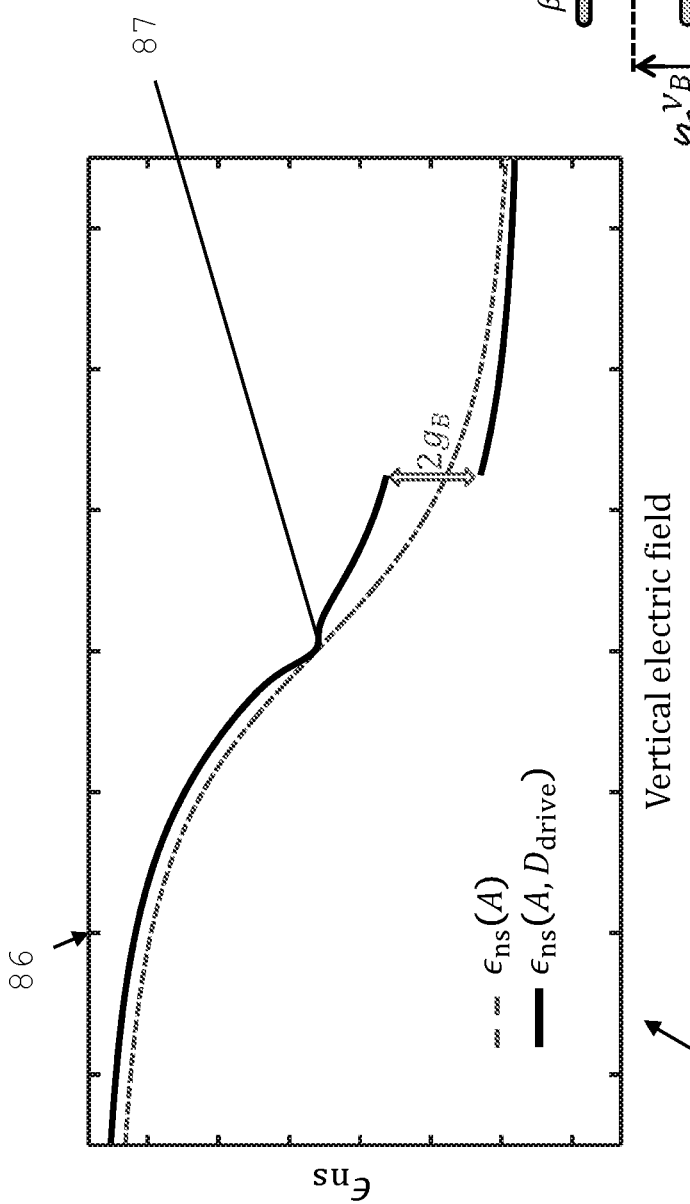
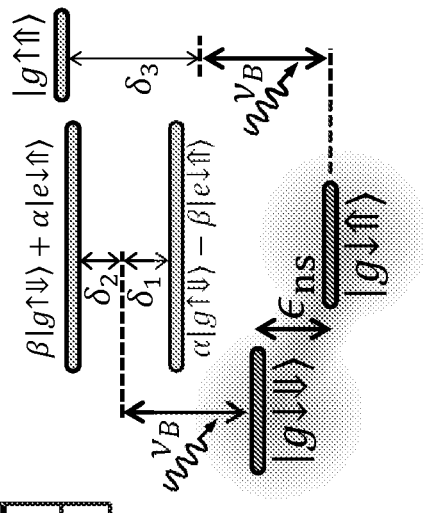
FIGURE 8(a)
FIGURE 8(b)

90 

92 - Applying a continuous magnetic field to the quantum processing elements to separate spin states associated with an electron and a nucleus of the donor atoms 94 - Applying an electric signal to each of the conductive electrodes to displace the electrons and create two electric dipoles associated with the respective processing elements to enable coupling of the quantum states of the two quantum bits associated with the two processing elements

112 - Applying a continuous magnetic field to the quantum processing elements to separate spin states associated with an electron and a nucleus of the donor atoms 114 - Applying an oscillating magnetic field which oscillates at a frequency close to a Zeeman frequency of the electron to each of the processing elements 116 - Applying an electric signal to each of the conductive electrodes to displace the electrons and create two electric dipoles associated with the respective processing elements and enable coupling of the quantum states of the two quantum bits associated with the two processing elements

152 - Applying a continuous magnetic field to the quantum processing elements to separate spin states associated with an electron and a nucleus of the donor atoms

154 - Confining electromagnetic field modes into a spatial region in proximity of the processing elements in a manner such that a quantized electric field is induced in the region between the interface and the donor atom to modulate a hyperfine interaction between the electron and the nucleus of each processing element and couple the quantum state of a quantum bit associated with a pair of electron-nuclear spin eigenstates of one processing element to a quantum bit associated with a pair of electron-nuclear spin eigenstates of the other processing element

FIGURE 15

160 

162 – Applying a continuous magnetic field to the quantum processing elements to separate spin states associated with an electron and a nucleus of the donor atoms 164 – Applying an oscillating magnetic field which oscillates at a frequency close to a Zeeman frequency of the electron to each of the processing elements 166 – confining electromagnetic field modes into a spatial region in proximity of the processing elements in a manner such that a quantized electric field is induced in the region between the interface and the donor atom to modulate a hyperfine interaction between the electron and the nucleus of each processing element and couple the quantum state of a quantum bit associated with a nuclear spin of one processing element to a quantum bit associated with a nuclear spin of the other processing element

FIGURE 16

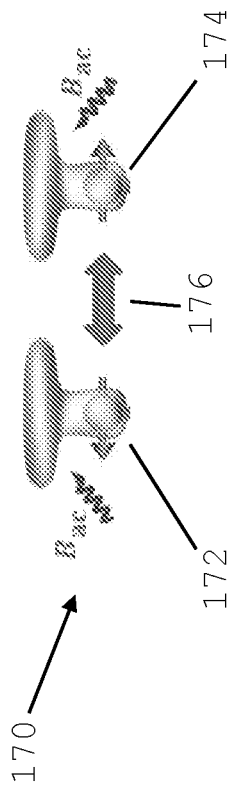
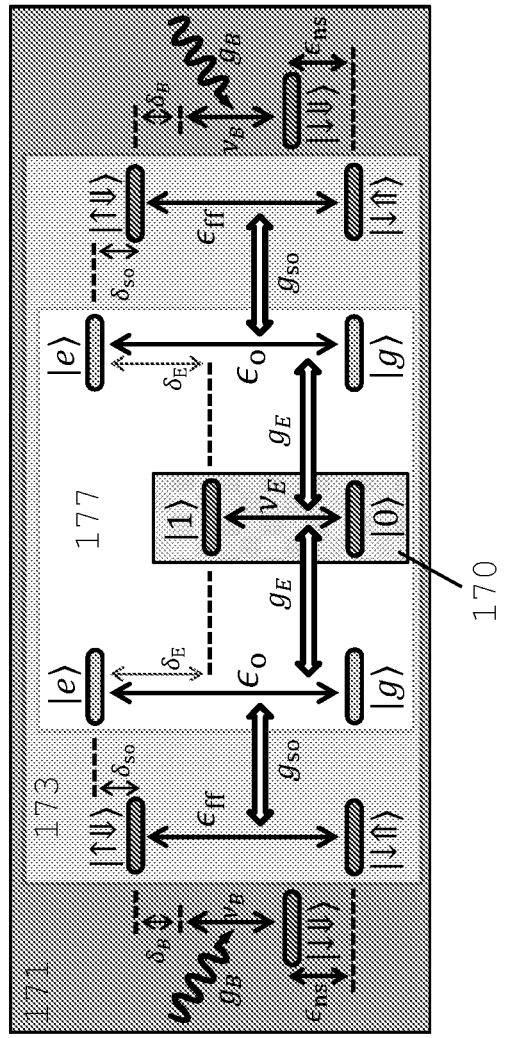
FIGURE 17(a)
FIGURE 17(b)

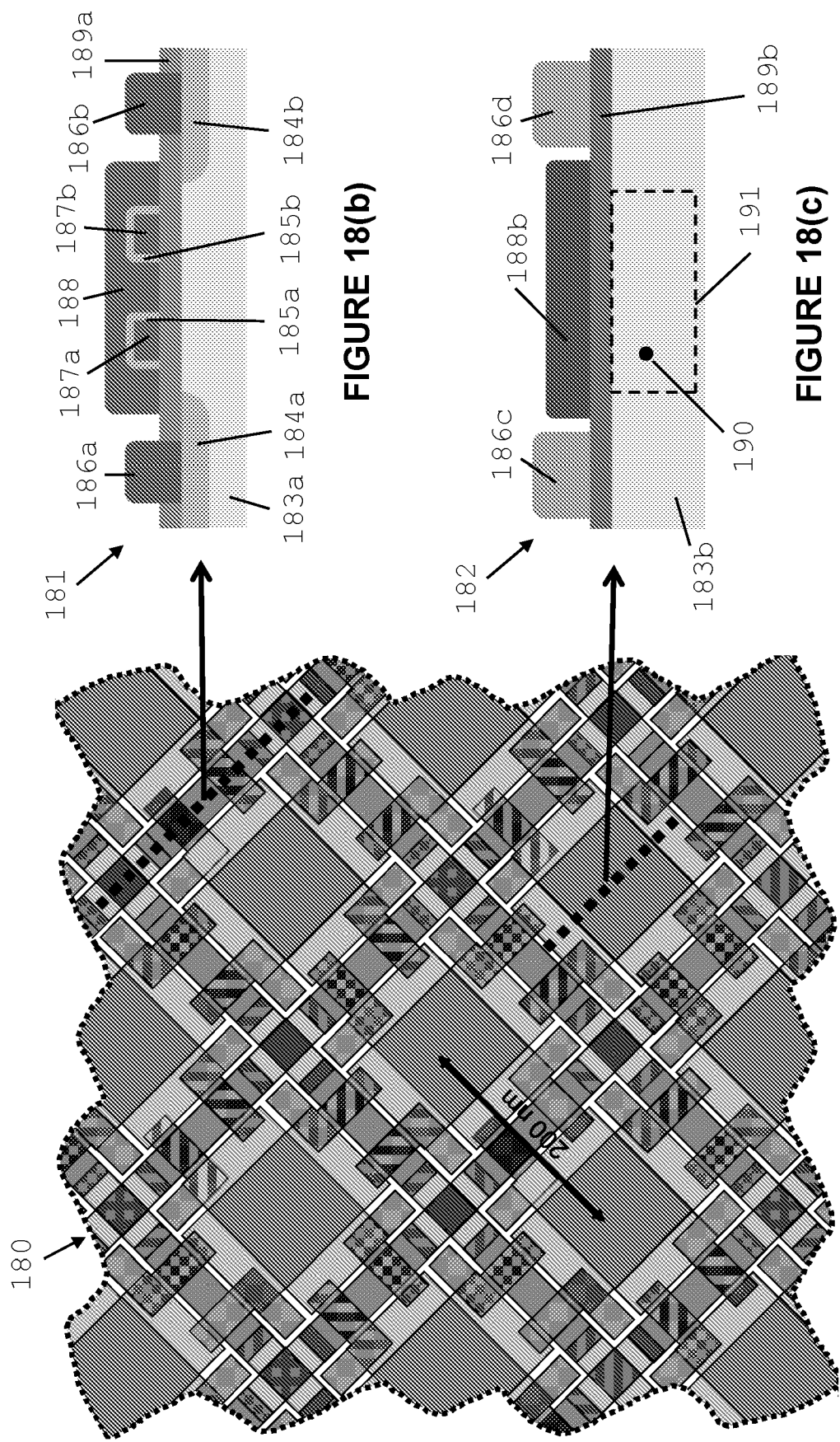

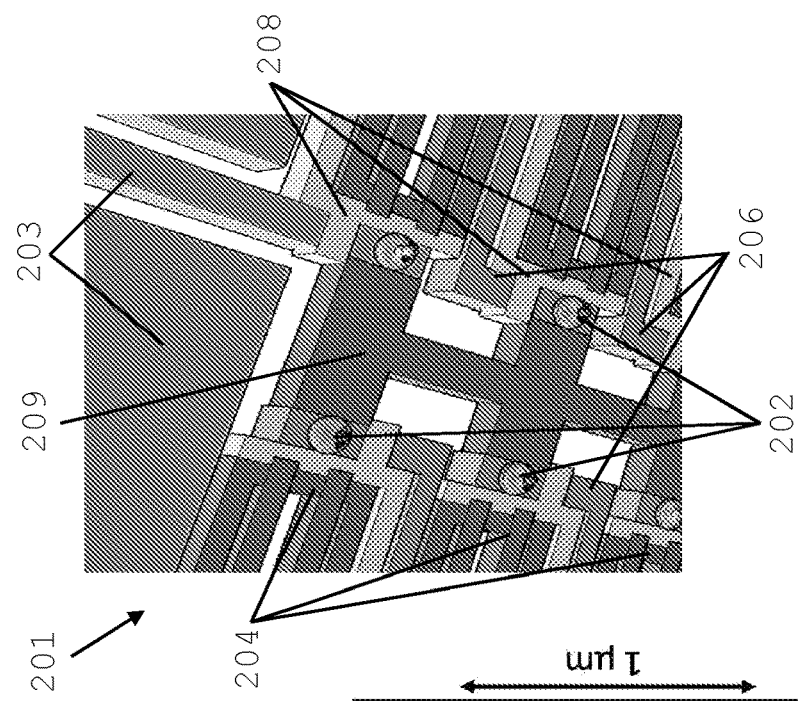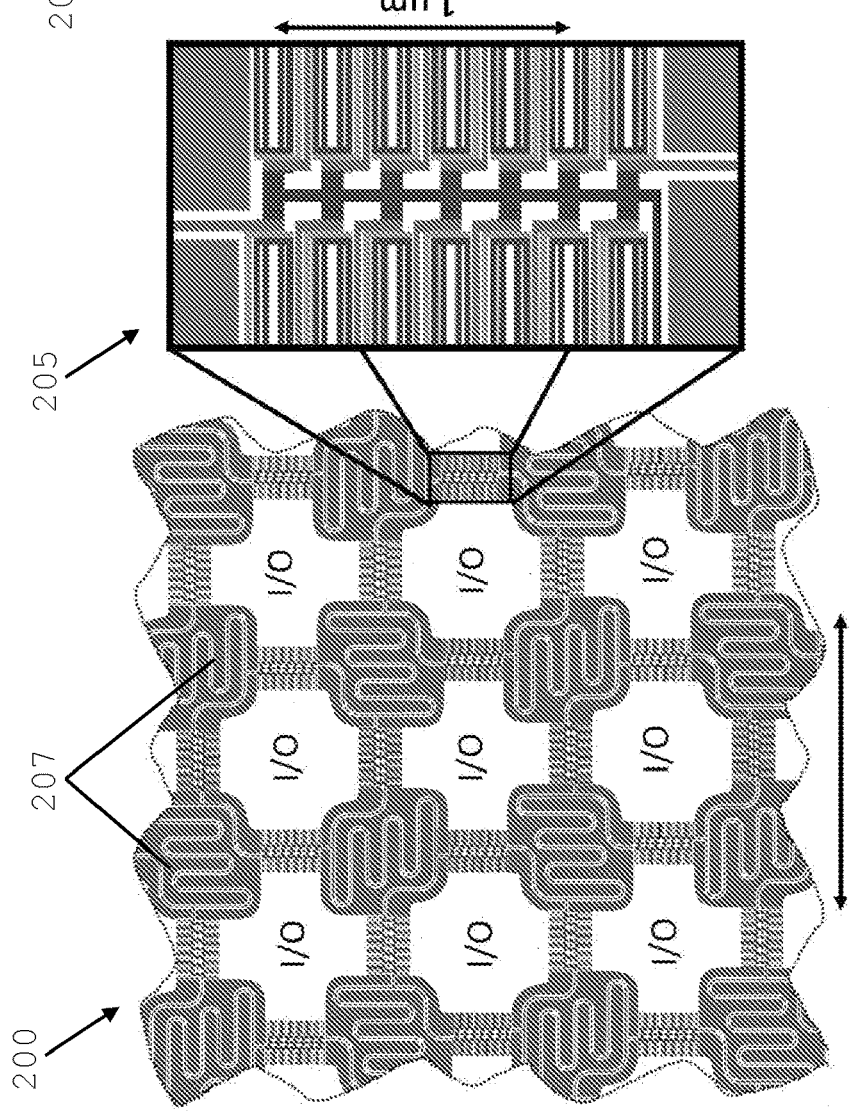
FIGURE 20(a)
FIGURE 20(b)

QUANTUM PROCESSING APPARATUS AND A METHOD OF OPERATING A QUANTUM PROCESSING APPARATUS

FIELD OF THE INVENTION

The present invention relates to a method of operation of a quantum processing element and an advanced processing apparatus comprising a plurality of quantum processing elements operated in accordance with the method.

BACKGROUND OF THE INVENTION

The power and capacity of computing components such as microprocessors and memory circuits has been increasing for the last 50 years, as the size of the functional units, such as transistors, has been decreasing. This trend is now reaching a limit, however, as it is difficult to make the current functional units (such as MOSFETs) any smaller without affecting their operation.

The technology employed to manufacture conventional silicon integrated circuits is today well established. Current microprocessors feature several hundreds of millions of transistors which are manufactured in high throughput lines.

Developments are ongoing to implement new types of advanced processing apparatuses that can implement powerful computations exploiting the rules of quantum mechanics. Such advanced processing apparatuses promise computational capacities well beyond current devices for a specific range of algorithms. Approaches to the realisation of devices for implementing quantum bits (qubits), the basic computational unit of a quantum processor, have been explored with different levels of success. A workable quantum processor needs to be able to perform two-qubit operations with low-error thresholds and be scalable. For example, semiconductor based qubits have been developed and described in a number of earlier patent publications, including U.S. Pat. No. 6,472,681 (Kane), U.S. Pat. No. 6,369,404 (Kane). The operation of these qubits is based on the exploitation of the quantum effects of a single dopant atom in a silicon crystalline lattice and the interaction between qubits is mediated by electron exchange coupling.

One of the problems related to this model is that the exchange interaction between electrons decays exponentially with donor separation and is highly dependent on the precise placement of the donors within a single lattice site, due to the oscillatory profile of the electron wave-function. The successful implementation of this architecture requires positioning of donors, separated by only 15 nm, with sub-nm precision. Such a level of precision makes the fabrication of the architecture very challenging, as discussed for example in U.S. Pat. No. 7,547,648 (Ruess et al.).

It has also been proposed to encode quantum information using the spin states of semiconductor quantum dots (Loss and DiVincenzo (Loss, DiVincenzo, DP quantum computation with quantum dots. Phys Rev. A56, 120; 1998).). This proposal primarily envisaged the use of quantum dots formed using electrostatic gates on a GaAs/AlGaAs heterostructure. However, the limited coherence time and the associated fidelity of the quantum state in these systems represent a significant hurdle to application of quantum dots in a quantum processor. Experimental work has been done in GaAs/AlGaAs on quantum dot qubits, but to realise large-scale arrays of such structures will require new manufacturing process technologies to be developed. More importantly, these materials suffer from problems with fidelity and dephasing time due to the presence of nuclear spins that are inherent to the GaAs crystal lattice.

Superconducting qubits have recently achieved low-error performance and a promising scalability. These qubits however have a macroscopic size (hundreds of micrometres scale) which prevents architectures from being fabricated with a large number of qubits within a small chip size. The large size, combined with the operation a GHz frequencies, can pose challenges in controlling the electromagnetic modes of a large number of qubits hosted in a cavity wider than the wavelength of the electromagnetic fields.

SUMMARY OF THE INVENTION

Embodiments of the invention propose a method to manipulate spin qubits with electric fields. The qubits manipulated in accordance with the method can be separated by hundreds of nanometres while preserving coupling capabilities. This substantially relaxes the precision requirements for fabrication. Advantageously, the schemes are compatible with the accuracy in donor placement achieved with ion implantation, as well as with scanning tunnelling microscope lithography.

In accordance with a first aspect, the present invention provides a method of operation of a quantum processing element, the processing element comprising:
  a semiconductor and a dielectric material forming an interface with the semiconductor;
  a donor atom embedded in the semiconductor at a distance from the interface; and
  a conductive electrode disposed on the dielectric material;
  the method comprising the steps of:
  applying a magnetic field to the quantum processing element to separate the energy of the spin states associated with an electron and a nucleus of the donor atom; and
  applying an electric field in the region between the interface and the donor atom to modulate a hyperfine interaction between the electron and the nucleus and control the quantum state of a quantum bit associated with a pair of electron-nuclear spin eigenstates of the electron and the nucleus.

The pair of electron-nuclear spin eigenstates comprises the 'electron spin up-nuclear spin down' and 'electron spin down-nuclear spin up' eigenstates. This type of qubit can be referred to as flip-flop qubit.

The electric field in the region between the interface and the donor atom may be applied by applying an oscillating electric signal to the electrode. The electrode may be an independent electrode or part of a structure suitable for addressing multiple processing elements.

In an embodiment, the frequency of the oscillating electric signal is selected based on the amplitude of the applied continuous magnetic field. This frequency may be also selected to be equal to an excitation frequency of the quantum bit and detuned from the orbital excitation frequency of the electron to prevent orbital excitation of the electron. The energy difference between the orbital states of the electron, and therefore the electron orbital excitation frequency, depends sensitively on the depth of the electron from the interface between the semiconductor and the dielectric material, because the electron can be displaced from the donor to the interface by the electric field applied in its vicinity.

In an embodiment, the oscillating electric signal and the magnetic field may be applied simultaneously to induce a transition in the quantum state of the quantum bit.

In an embodiment, the method further comprises the step of applying an oscillating magnetic field to the processing element to transfer the quantum state associated with the pair of electron-nuclear spin eigenstates to a quantum state associated with the nuclear spin to implement a nuclear spin quantum bit.

In accordance with a second aspect, the present invention provides a method of operation of a quantum processing element, the processing element comprising:
- a semiconductor and a dielectric material forming an interface with the semiconductor;
- a donor atom embedded in the semiconductor at a distance from the interface; and
- a conductive electrode disposed on the dielectric material; the method comprising the steps of:
- applying a continuous magnetic field to the quantum processing element to separate spin states associated with an electron and a nucleus of the donor atom;
- applying an oscillating magnetic field which oscillates at a frequency close to a Zeeman frequency of the electron; and
- applying an electric field in the region between the interface and the donor atom to modulate a hyperfine interaction between the electron and the nucleus and control the quantum state of a quantum bit associated with the spin of the nucleus;
- wherein the frequency of the oscillating magnetic field is selected based on the frequency of the oscillating electric signal.

This type of qubit can be referred to as nuclear-spin qubit. One advantage of using the nuclear-spin as a qubit is that it has a long coherence time since it is less prone to electromagnetic interaction with the external environment.

In an embodiment, the frequency of the oscillating magnetic field is selected to be detuned from the electron spin excitation frequency to prevent flipping of the electron spin quantum state.

In an embodiment, the oscillating electric signal and oscillating magnetic field are applied simultaneously to induce a transition in the quantum state of the nuclear spin quantum bit.

In embodiments, the frequency of the oscillating magnetic field is selected to be smaller than the frequency of the oscillating electric signal by an amount equal to a nuclear spin Zeeman frequency.

Embodiments of the method of the first aspect or the method of the second aspect comprises the step of applying a biasing DC electric signal to the electrode to bias the electron in a region where the hyperfine interaction is highly sensitive to small variations in the electric field. This may be attained by displacing the electron wave function such that it spans an extended region between the donor nucleus and the interface between the semiconductor and the dielectric.

A biasing electric signal may be applied to the electrode to bias the electron in a region in proximity of the interface or in a region close to the nucleus to minimise an interaction of the quantum state of the quantum bit with an external electromagnetic environment.

In some embodiments, the method further comprises the step of applying an electric bias to the conductive electrode to displace the electron and create an electric dipole associated with the processing element. The dipole created can interact with another electric dipole of another processing element via dipole-dipole interaction to allow interaction of the quantum states of two processing elements and coupling of two qubits. In order to allow controllable coupling, the electrical bias may be maintained for a predetermined period of time, and then switched off.

In some embodiments, the method further comprises the steps of confining electromagnetic field modes into a spatial region in proximity of the processing element. An arrangement for confining electromagnetic modes may be disposed in proximity of the processing element. The electromagnetic field modes may be quantized to comprise zero, one, or more photons. The interaction of the quantized electromagnetic field modes and the electron may be used to enable coupling of the zero, one or more photons to the quantum state of the quantum bit.

The arrangement used for confining electromagnetic modes may be a resonator, such as a microwave resonating cavity or a coplanar waveguide resonator. The state of the quantum bit may be read-out by measuring the shift in the resonance frequency of the resonator caused by the coupling of the photon(s) to the qubit.

The quantized modes of the zero, one or more photons may be spatially extended through the resonator, such that the electromagnetic fields associated with the photon modes overlap with multiple quantum bits, enabling long distance quantum bit coupling. This coupling mechanism, intermediate by a photon, may be used to couple qubits which are at least 1 μm from each other, and up to a distance comparable with the wavelength of the photon.

In an embodiment, the method further comprises the step of detuning the processing element from the resonator modes to prevent decay of the quantum state of the quantum bit into a photon.

In accordance with the third aspect, the present invention provides a method of coupling quantum states of two processing elements, each of the processing elements comprising:
- a semiconductor and a dielectric material forming an interface with the semiconductor;
- a donor atom embedded in the semiconductor at a given distance from the interface; and
- a conductive electrode disposed on the dielectric material; the method comprising the steps of:
- applying a continuous magnetic field to the quantum processing elements to separate spin states associated with an electron and a nucleus of the donor atoms; and
- applying an electric signal to each of the conductive electrodes to displace the electrons and create two electric dipoles associated with the respective processing elements to enable coupling of the quantum states of the two quantum bits associated with the two processing elements.

In accordance with the fourth aspect, the present invention provides a method of coupling quantum states of two processing elements, each of the processing elements comprising:
- a semiconductor and a dielectric material forming an interface with the semiconductor;
- a donor atom embedded in the semiconductor at a given distance from the interface; and
- a conductive electrode disposed on the dielectric material; the method comprising the steps of:
- applying a continuous magnetic field to the quantum processing elements to separate spin states associated with an electron and a nucleus of the donor atoms;
- applying an oscillating magnetic field which oscillates at a frequency close to a Zeeman frequency of the electron to each of the processing elements; and
- applying an electric signal to each of the conductive electrodes to displace the electrons and create two electric dipoles associated with the respective processing elements to enable coupling of the quantum states of the two quantum bits associated with the two processing elements.

In some embodiments, the two processing elements are disposed at least 150 nm apart.

In accordance with the fifth aspect, the present invention provides a method of coupling quantum states of two processing elements, each of the processing elements comprising:
- a semiconductor and a dielectric material forming an interface with the semiconductor;
- a donor atom embedded in the semiconductor at a given distance from the interface; and
- a conductive electrode disposed on the dielectric material; the method comprising the steps of:
- applying a continuous magnetic field to the quantum processing elements to separate spin states associated with an electron and a nucleus of the donor atoms; and
- confining electromagnetic field modes into a spatial region in proximity of the processing elements in a manner such that a quantized electric field is induced in the region between the interface and the donor atom to modulate a hyperfine interaction between the electron and the nucleus of each processing element and couple the quantum state of a quantum bit associated with a pair of electron-nuclear spin eigenstates of one processing element to a quantum bit associated with a pair of electron-nuclear spin eigenstates of the other processing element.

In accordance with the sixth aspect, the present invention provides a method of coupling quantum states of two processing elements, each of the processing elements comprising:
- a semiconductor and a dielectric material forming an interface with the semiconductor;
- a donor atom embedded in the semiconductor at a given distance from the interface; and
- a conductive electrode disposed on the dielectric material; the method comprising the steps of:
- applying a continuous magnetic field to the quantum processing elements to separate spin states associated with an electron and a nucleus of the donor atoms;
- applying an oscillating magnetic field which oscillates at a frequency close to a Zeeman frequency of the electron to each of the processing elements; and
- confining electromagnetic field modes into a spatial region in proximity of the processing elements in a manner such that a quantized electric field is induced in the region between the interface and the donor atom to modulate a hyperfine interaction between the electron and the nucleus of each processing element and couple the quantum state of a quantum bit associated with a nuclear spin of one processing element to a quantum bit associated with a nuclear spin of the other processing element;
- wherein a frequency of the oscillating magnetic field is selected based on a resonance frequency of the quantized electromagnetic field.

In the fifth and sixth aspect, the two processing elements may be disposed at least 1 μm apart. The two processing elements may be disposed in the proximity of a resonator and be tuned in resonance with each other while detuned from the resonator mode. In this way respective quantum bits are coupled via virtual photons.

The quantum state of the two quantum bits can be controlled by of applying an electrical signal to the electrodes. The electrical signal may be applied simultaneously for the two processing elements or sequentially to one qubit before the other, to set the two quantum states.

Conductive electrodes may be used to bias the electrons in a region in proximity of the interface or close to the nucleus to minimise the interaction of the quantum state of each quantum bit with an external electromagnetic environment and minimise coupling between the two quantum bits. The biasing electrodes may be separate electrodes to the electrodes used to control the quantum states.

The biasing of the electrons may be performed before or after the coupling takes place. In some embodiments the electrons are normally kept at the interface between semiconductor and dielectric, away from the donor, unless a coupling operation is being performed.

In accordance with a seventh aspect, the present invention provides an advanced quantum processing apparatus, comprising a plurality of processing elements disposed in an electromagnetic resonator; each of processing elements comprising:
- a semiconductor and a dielectric material forming an interface;
- a donor atom embedded in the semiconductor at a given distance from the interface;
- a conductive electrode disposed on the dielectric material;
- wherein each processing element is disposed in relation to the electromagnetic resonator in a manner such that an electromagnetic field mode in the resonator induces a quantized electric field in the region between the interface and the donor atom and couples to the quantum state of a quantum bit associated with a pair of electron-nuclear spin eigenstates of the electron and the nucleus.

In accordance with an eight aspect, the present invention provides an advanced processing apparatus, comprising a plurality of processing elements disposed in an electromagnetic resonator; each of processing elements comprising:
- a semiconductor and a dielectric material forming an interface;
- a donor atom embedded in the semiconductor at a given distance from the interface;
- a conductive electrode disposed on the dielectric material;
- wherein each processing element is disposed in relation to the electromagnetic resonator in a manner such that an electromagnetic field mode in the resonator induces a quantized electric field in the region between the interface and the donor atom and couples to the quantum state of a quantum bit associated with a nuclear spin of one or more of the processing elements.

In an embodiment, each processing element is disposed in relation to the electromagnetic resonator in a manner such that an electromagnetic field mode in the resonator induces a modulation of the hyperfine interaction between the electron and the nucleus of one or more of the processing elements.

In embodiments, the two processing elements are disposed at least 1 μm apart. The resonator may comprise a microwave resonating cavity or a coplanar waveguide resonator.

In embodiments, the coplanar waveguide resonator comprises one or more discontinuities and the distance between the discontinuities is selected based on the desired frequency of the quantized electric field induced the region between the interface and the donor atom.

In accordance with the ninth aspect, the present invention provides an advanced processing apparatus, comprising a plurality of processing elements disposed in a two-dimensional arrangement; each of processing elements comprising:
- a semiconductor and a dielectric material forming an interface;
- a donor atom embedded in the semiconductor at a given distance from the interface;
- a conductive electrode disposed on the dielectric material;
- wherein one or more processing elements are operated in accordance with the method of the first aspect.

In embodiments, the processing elements may coupled to each other in accordance with the method of the second, third or fourth aspect.

Embodiments of the apparatus can be manufactured using a CMOS process.

Advantageous embodiments of the present invention provide methods to couple spins to electric fields, mediated by the charge state of an electron in an advanced processing apparatus comprising MOS-like processing elements including a buried donor atom.

The spin qubits can be controlled using electrical means. Qubits can be associated electron-nuclear spin states of the dopant atom or nuclear spin states. Nuclear spin qubits can be defined using an oscillating magnetic field. Using isotopically enriched $^{28}$silicon as semiconductor substrate for the processing elements, the method allows the combination of long coherence times of nuclear-spin qubits with fast manipulation speeds of charge qubits. Advantageously, 2-qubit coupling can be implemented via direct electric dipole-dipole interaction between processing elements. This interaction can reach longer distances than direct spin-spin interaction and drastically relaxes the fabrication precision demands for developing a spin-based quantum computer. Electric dipoles for the processing elements are created using an electrical biasing signal which can be applied via the same electrode which is used to manipulate the quantum state or a separate biasing electrode.

Another advantage of the method is provided by the possibility of coupling the quantum states of qubits to single microwave photons, including the nuclear-spin qubit. This is a remarkable advantage given the small magnetic dipole and gyromagnetic moment of nuclear spins and their usual insensitivity to electric fields. The method opens new possibilities for coupling nuclear-spin qubits at long distances and also for non-demolition read-out via a microwave resonator.

An advantageous architecture to implement the method is also disclosed. In this architecture a microwave resonator is coupled to the processing elements. The microwave resonator may function as main electrical electrode to control the quantum state of the qubits. It also allows coupling the quantum state of the microwave photons with the quantum state of the qubit, and to use the photons to mediate the coupling between several quantum bits throughout the architecture.

BRIEF DESCRIPTION OF THE DRAWINGS

Features and advantages of the present invention will become apparent from the following description of embodiments thereof, by way of example only, with reference to the accompanying drawings, in which;

FIGS. 3 and 6 are flow diagrams of methods for operating a quantum processing element;

FIG. 4 shows a Bloch sphere of an electron-nuclear spin system coupled to and electric field via hyperfine interaction A (a), a schematic representation of the donor and partially ionized electron wavefunction, both with their spin arrows, and an AC electric drive (b), and an energy level diagram of a 'flip-flop' qubit driven using an AC electric field (c);

FIG. 8 shows the nuclear spin qubit transition frequency, when subject to an AC magnetic drive, dependence on applied electric field (a) and the corresponding energy level diagram (b);

FIGS. 9, 11, 15 and 16 are flow diagrams of methods for operating two quantum processing elements;

FIG. 17 shows a schematic spatial visualization of two nuclear spin qubit gates via a common photon (a) and the corresponding energy level diagram (b);

FIG. 18 is a schematic top-view (a) and lateral cross-sections (b) and (c) representation of a quantum processor in accordance with embodiments;

FIG. 20 shows schematic top-view (a) and bottom-view zoom-in (b) representations of a quantum processor in accordance with embodiments.

DETAILED DESCRIPTION OF EMBODIMENTS

In the following description a method for operating a processing element or a pair of processing elements in accordance with embodiments is described.

Figure 1A:
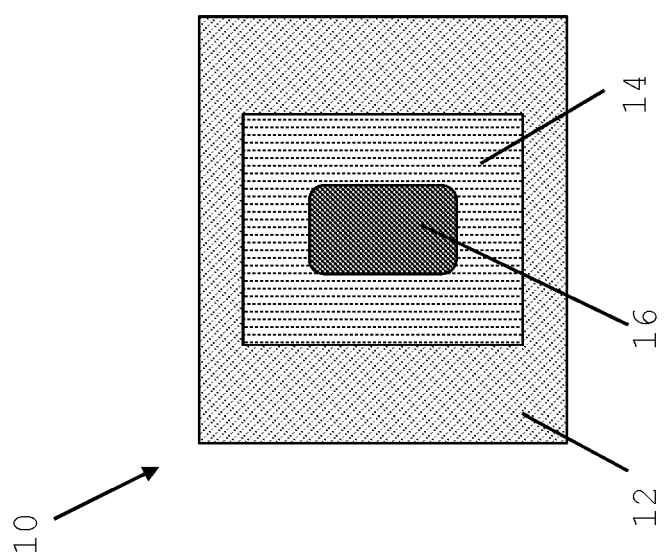
FIG. 1 is a schematic illustration of a top view (a) and a side cross-sectional view (b) of a single processing element.
Figure 1B:
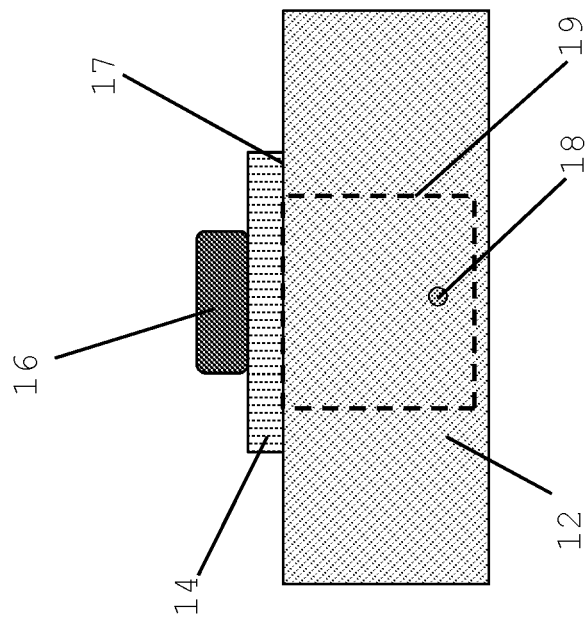

Referring to FIG. 1, there is shown a processing element 10 which can be operated using a method in accordance with embodiments. FIG. 1(a) is a top view of the processing element and FIG. 1(b) is a side cross-section. The processing element 10 may be used as a qubit element for a quantum computer comprising a plurality of these processing elements. Processing element 10 comprises a semiconductor substrate 12 and a dielectric 14, in this example being $^{28}$silicon and silicon dioxide respectively and forming a Si/SiO$_2$ interface 17. A donor atom 18 is located within the substrate 12 inside region 19 under gate 16. The donor can be introduced into the substrate using nano-fabrication techniques, such the hydrogen lithography provided by scanning-tunneling-microscopes, or the industry-standard ion implantation techniques. Processing element 10 includes a single atom 18 embedded in the silicon crystal. However, the methods described herein may be applied to processing elements including clusters of more than one embedded atom.

A gate electrode 16 is located above region 19 and is operable to interact with the donor atom 18. For example, gate 16 may be used to induce an AC electric field in the region between the interface 17 and the donor atom 18 to modulate a hyperfine interaction between the electron and the nucleus.

The electric field can be used to control the quantum state of a quantum bit associated with the pair of electron-nuclear spin eigenstates 'electron spin up-nuclear spin down' and 'electron spin down-nuclear spin up'. This type of qubit is referred to herein as 'flip-flop qubit'.

Alternatively, the AC electric field can be used to control the quantum state of a quantum bit associated with a spin of the nucleus, 'nuclear-spin' qubit herein. In this case the AC electric filed works in synergy with an applied oscillating magnetic field.

Figure 2:
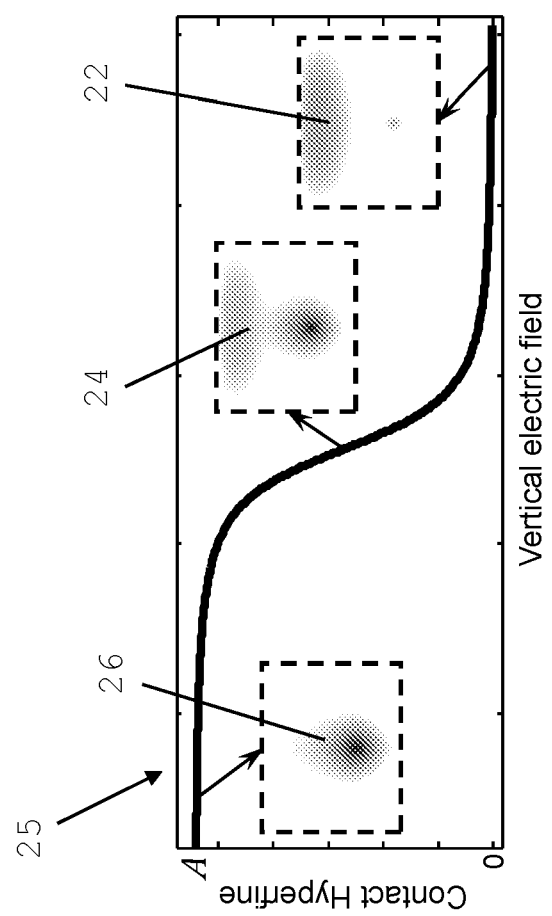
FIG. 2 is a schematic plot of the hyperfine interaction between the electron and the nucleus as a function of the electric field with insets illustrating the wavefunction of an electron associated with the donor atom for different values of the electric field.

FIG. 2 shows a plot 25 of the hyperfine interaction between the electron and the nucleus as a function of the electric field resulting from the voltage applied to electrode 16. Insets 22, 24 and 26 show the electron wavefunction, inside region 19, under different vertical electric fields, arising from an electrical signal applied to gate 16. Electrode 16 therefore controls the position of the electron in the region between the nucleus and the interface 17.

A biasing electric signal can be applied to bias the electron in a region in proximity of the interface (as shown in inset 22), or in a region close to the nucleus (as shown inset 26), to minimise an interaction of the quantum state of the quantum bit with an external electromagnetic environment.

Furthermore a biasing electric signal can be applied to position the electron in a region of high sensitivity of the hyperfine interaction to the electric field. In this region, approximately half of the electron density resides at the interface, and the other half at the embedded donor atom (as shown in inset 24).

Electrode 16 may be used to apply an AC electrical signal to interact with the quantum state of the qubit.

Processing element 10 only shows one electrode 16 used to apply the biasing electrical signal and the AC electrical signal. However, in a variation of processing element 10 separate electrodes can be used.

Donor atom 18 may be a phosphorous atom embedded in an isotopically pure $^{28}$Si crystal at a depth $z_d$ from the interface with a thin $SiO_2$ layer. The orbital wave-function $\Psi$ of the donor-bound electron can be controlled by a vertical electric field $E_z$ applied by metal gate 16. It changes from a bulk-like donor state at low electric fields to an interface-like state at high-fields.

The hyperfine interaction $A(E_z)$, proportional to the square amplitude of the electron wave-function at the donor site, changes accordingly from the bulk value A≈117 MHz to A≈0 when the electron is fully displaced to the interface. At the ionization point, where the electron is shared halfway between donor and interface, A(Ez) can vary strongly upon the application of a small voltage on the top gate. Shifting the electron wave-function from the donor to the interface also results in the creation of an electric dipole $\mu_e$=ed, where e is the electron charge and d is the separation between the mean positions of the donor-bound and interface-bound wave-functions. The induced electric dipole is one of the important features exploited in embodiments of the invention described herein.

Referring now to FIG. 3 there is shown a flow-diagram 30 with the basic steps used for operating the quantum processing element. At step 32 a magnetic field is applied to the quantum processing element to separate spin states associated with an electron and a nucleus of the donor atom. At step 34 an electric field is induced in the region between the interface and the donor atom to modulate a hyperfine interaction between the electron and the nucleus and control the quantum state of a quantum bit associated with a pair of electron-nuclear spin eigenstates of the electron and the nucleus.

FIG. 4(a) shows a Bloch sphere 40 of an electron-nuclear spin system coupled to an electric field via hyperfine interaction A(E). To perform quantum state manipulations a magnetic field is also applied to the processing element to separate spin states associated with an electron and a nucleus of the donor atom. Under an applied magnetic field $B_0$, the spin Hamiltonian reads:

$$\mathcal{H}_{spin} = \mathcal{H}_{B_0} + \mathcal{H}_A \tag{1}$$

$$\mathcal{H}_{B_0} = B_0(\gamma_e S_z - \gamma_n I_z) \tag{2}$$

$$\mathcal{H}_A = AS \cdot I \tag{3}$$

Here $\gamma_e$ and $\gamma_n$ are the electron and nucleus gyromagnetic ratios, respectively, and A is the hyperfine coupling. $S=(S_x, S_y, S_z)$ and $I=(I_x, I_y, I_z)$ are the electron and nucleus spin operators, respectively. In silicon, $\gamma_e \approx 28$ GHz/T, whereas $\gamma_n$ and A depend on the donor type according to Table 1.

TABLE 1

Nuclear spin I, hyperfine coupling A and nuclear gyromagnetic ratio $\gamma_n$ of different donors in silicon.

| Donor | I | A [MHz] | $\gamma_n$ [MHz/T] |
|---|---|---|---|
| $^{31}$P | 1/2 | 117 | 17.2 |
| $^{75}$As | 3/2 | 198 | 7.3 |
| $^{121}$Sb | 5/2 | 187 | 10.3 |
| $^{123}$Sb | 7/2 | 101 | 5.6 |
| $^{209}$Bi | 9/2 | 1475 | 7.1 |

For simplicity, we consider a nuclear spin I=½, which can be that of a $^{31}$P donor. The Hamiltonian $\mathcal{H}_{B_0}$ defines electron-nuclear spin eigenstates $|\uparrow\Uparrow\rangle$, $|\downarrow\Downarrow\rangle$, $|\downarrow\Uparrow\rangle$ and $|\uparrow\Downarrow\rangle$, whereas $\mathcal{H}_A$ defines $|\uparrow\Uparrow\rangle$, $|\downarrow\Downarrow\rangle$, $(|\downarrow\Uparrow\rangle - |\uparrow\Downarrow\rangle)/\sqrt{2}$ and $(|\downarrow\Uparrow\rangle + |\uparrow\Downarrow\rangle)/\sqrt{2}$. Under strong enough magnetic fields ($\gamma_+ B_0 \gg A$, where $\gamma_+ = \gamma_e + \gamma_n$), the subspace $|\uparrow\Downarrow\rangle$ and $|\downarrow\Uparrow\rangle$ are approximately eigenstates of the system, with frequency separation:

$$\epsilon_{ff}(A) = \sqrt{(\gamma_+ B_0)^2 + [A(E_z)]^2} \approx \gamma_+ B_0 \tag{4}$$

This subspace is referred to herein as the 'flip-flop' qubit. The hyperfine interaction AS·I is a transverse term in the flip-flop basis. Controlling A via electrical means opens up new ways for electron-nuclear spins control. Modulating $A(E_z)$ at the frequency $\epsilon_{ff}(A)$, causes an electric dipole spin resonance (EDSR) transition between the $|\downarrow\Uparrow\rangle$, $|\uparrow\Downarrow\rangle$ basis states. A conceptually similar mechanism is involved in the resonant drive of a 3-electron, 2-dot hybrid qubit.

In FIG. 1, the electrical signal applied to gate 16 can create a strong vertical electric field that pulls the electron wavefunction from the donor 18 towards interface 17. Since the hyperfine coupling is proportional to the electron orbital wavefunction $|\psi|^2$ at the donor site, it abruptly shifts from its maximum value to zero when the electron is ionized to the interface, as shown in FIG. 2(b). The intermediate situation, in which the electron is equally shared between donor and interface, is the best point to control the spin state via an electrical signal applied to electrode 16. Here the hyperfine interaction has its strongest variation. FIG. 4 schematically depicts such an optimal operation.

The orbital wave function of the electron in this scenario can be approximated as a two level system, $|d\rangle$ for the electron at the donor, and $|i\rangle$ for the electron at the interface. At the intermediate location, the eigenstates $|g\rangle=(|d\rangle-|i\rangle)/\sqrt{2}$ and $|e\rangle=(|d\rangle+|i\rangle)/\sqrt{2}$ are separated by an energy difference equal to the tunnel coupling $V_t$, according to the Hamiltonian, in the $|d\rangle$, $|i\rangle$ basis:

$$\mathcal{H}_{orb} = \frac{v_t \sigma_x - [e(E_z - E_z^0)d/h]\sigma_z}{2}, \quad (5)$$

where $\sigma_z$ and $\sigma_x$ are Pauli matrices. The electron vertical position is represented by the Pauli $\sigma_z$ operator, where we assume $\langle\sigma_z\rangle=-1$ for the electron at the donor and $\langle\sigma_z\rangle=+1$ for the electron at the interface. The hyperfine coupling is then dependent on the electron orbital position according to:

$$\mathcal{H}_A^{orb} = A\left(\frac{1-\sigma_z}{2}\right)S \cdot I \quad (6)$$

The electron ground $|g\rangle$ and excited $|e\rangle$ orbital eigenstates depend on $E_z - E_z^0$ and have an energy difference given by:

$$\epsilon_o = \sqrt{(V_t)^2 + [e(E_z - E_z^0)d/h]^2}$$

This results in a transverse coupling $g_{so}$ between the flip-flop qubit and the electron charge states:

$$g_{so} = \frac{A}{4}\frac{V_t}{\varepsilon_o} \quad (7)$$

A vertical electric field of amplitude $E_{ac}$, oscillating at a frequency $v_E$ equal $\epsilon_0$, would drive transitions between the charge eigenstates at a rate (half Rabi-frequency).

$$g_E = \frac{eE_{ac}d}{4h}\frac{V_t}{\varepsilon_o}. \quad (8)$$

An electrical modulating signal applied to electrode 16 that modulates A at a frequency equal to $\epsilon_{ff}(A)$ can be used to drive the qubit between $|\uparrow\Downarrow\rangle$ and $|\downarrow\Uparrow\rangle$, at a Rabi frequency proportional to the modulation amplitude. This qubit gate can be achieved electrically by using an oscillating electric field, with frequency $v_E=\epsilon_{ff}(A)$, which periodically wiggles the electron between the donor and the interface. This orbital dynamics is described by the following Hamiltonian:

$$\mathcal{H}_E = \frac{eE_{ac}d\cos(2\pi v_E t)\sigma_z}{2h}, \quad (9)$$

where $E_{ac}$ is the electric field amplitude, d the donor-interface distance and h the Planck constant. The total Hamiltonian describing flip-flop drive by an AC electric field is:

$$\mathcal{H}_{drive} = \mathcal{H}_{B_0} + \mathcal{H}_A^{orb} + \mathcal{H}_{orb} + \mathcal{H}_E \quad (10)$$

FIG. 4(c) shows and an energy level diagram of a 'flip-flop' qubit driven using an AC electric field. In order to prevent excitation of the electron orbital state, and therefore suppress relaxation due to coupling to phonons, the state $|e\rangle$ is minimally excited, by choosing $\delta_{so} \gg g_{so}$ and $\delta_E \gg g_E$, where $\delta_E = \epsilon_o - v_E$. Under these conditions, and if $\delta_E = \delta_{so}$, the 'flip-flop' qubit is driven at a rate (half Rabi frequency), to second order:

$$g_E^{ff} = \frac{g_{so}g_E}{2}\left(\frac{1}{\delta_{so}} + \frac{1}{\delta_E}\right) \quad (11)$$

$\delta_E$ and $\delta_{so}$ may be selected to be large enough as to prevent electron orbital excitation, but not too large since this would reduce the flip-flop transition rate considerably. When a state excitation is to be prevented, the detuning ($\delta_E$ and $\delta_{so}$) may be selected to be at least 10 times the coupling rates to it ($g_E$ and $g_{so}$). This ensures less than 1% excitation probability of charge states.

As an example, for a $^{31}$P donor, $A/4 \approx 29$ MHz, which sets $\delta_E = \delta_{so} = 290$ MHz. If this donor is d=15 nm deep in the silicon, a maximum field of $E_{ac}=32$ V/m can be applied while still preventing orbital excitation ($g_E=29$ MHz). At this field, the flip-flop qubit is driven at a Rabi frequency of $1/t_{Rabi}=6$ MHz.

The magnetic field and electric signal can be applied simultaneously to drive the state of the 'flip-flop' quantum bit.

Electric field noise during electric drive may affect the qubit states in the presence of electric field noise. If the noise is such to affect the qubit states, the qubits can be operated at bias points that render the qubit precession frequency highly robust against noise.

Figure 5:
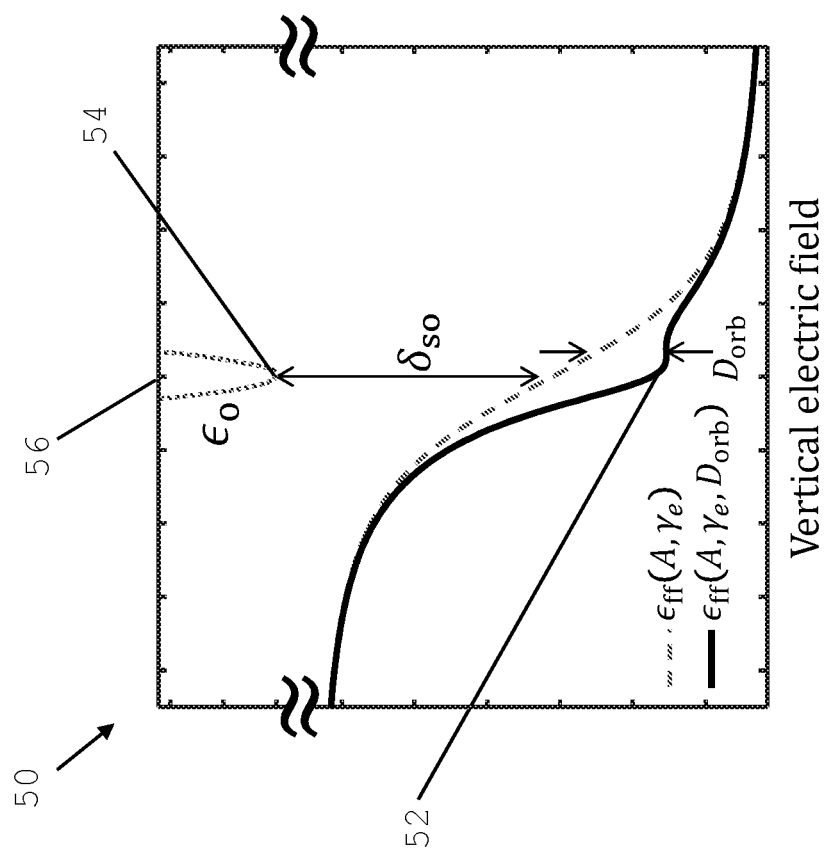
FIG. 5 shows the flip-flop qubit transition frequency dependence on applied electric field.

FIG. 5(a) shows a plot 50 with charge ($\epsilon_0$) and flip-flop ($\epsilon_{ff}$) qubits transition frequencies as a function of vertical electric field $E_z$. At the ionization point 56, the energy splitting of the charge qubit is minimum and equal to $V_t$ (region 54 in FIG. 5(a)), therefore first-order insensitive to electric noise. Also around the ionization point, the flip-flop qubit energy depends strongly on $E_z$, through the combined effect of the hyperfine interaction A, and the orbital dependence of the electron gyromagnetic ratio, $\gamma_e$:

$$\epsilon_{ff}(A,\gamma_e) = \sqrt{[\gamma_e(E_z)+\gamma_n]^2 B_0^2 + [A(E_z)]^2}, \quad (12)$$

shown in plot 50 (dashed line). The qubit transition frequency has an extra bend around the ionization point (full line in plot 50), when considering the dispersive coupling to the electron orbit. The resulting shift:

$$D_{orb}(E_z) = \frac{|g_{so}(E_z)|^2}{\delta_{so}(E_z)} \quad (13)$$

reduces the flip-flop qubit frequency to:

$$\epsilon_{ff}(A,\gamma_e,D_{orb}) = \epsilon_{ff}(A,\gamma_e) - D_{orb}(E_z), \quad (14)$$

This dispersive shift is largest around the ionization point, since $\delta_{so}$ is lowest (i.e. the charge qubit frequency comes closest to the flip-flop qubit, see dotted line in plot 50) and $g_{so}$ is highest.

Most importantly, by tuning $\delta_{so}$ the flip-flop qubit frequency dependence on electric field can be tuned, up to level in which a plateau 52 is formed. Around this region the qubit precession frequency is highly insensitive to electric noise, a property similar to 'clock transitions' found in, for example, atomic clocks.

In some embodiments, all quantum operations can be operation points as close as possible to the plateau regions 52 and 54, in such a way that effects from electric noise is minimum.

In some embodiments, an oscillating magnetic signal can be applied to the processing element to transfer the quantum state associated with the pair of electron-nuclear spin eigenstates to a quantum state associated with the nuclear spin to implement a nuclear spin quantum bit.

By coupling the hyperfine interaction to the electron position, the nuclear spin can be driven using electrical means. As discussed above, this process also flips the electron spin. According to some embodiments of the method, the nuclear spin can be controlled independently from the electron spin so that the qubit for the processing element can be associated with the nuclear spin to implement a 'nuclear-spin' qubit. One of the main advantages of the nuclear-spin qubit is the longer coherence time.

The nuclear-spin qubit can be driven by electric fields after applying an oscillating magnetic field, with frequency close to the electron Zeeman frequency, to couple the spins states $|\downarrow\Downarrow\rangle$ and $|\uparrow\Uparrow\rangle$.

Referring now to FIG. 6 there is shown a flow-diagram 60 with the basic steps used for operating the quantum processing element as a nuclear-spin qubit. At step 62 a continuous magnetic field is applied to the quantum processing element to separate spin states associated with an electron and a nucleus of the donor atom. At step 64 an oscillating magnetic field is applied to the processing element in a direction perpendicular to the continuous magnetic field. The magnetic field oscillates at a frequency close to a Zeeman frequency of the electron. At step 66 an electric field is induced in the region between the interface and the donor atom to modulate a hyperfine interaction between the electron and the nucleus and control the quantum state of the nuclear-spin qubit.

Figure 7B:
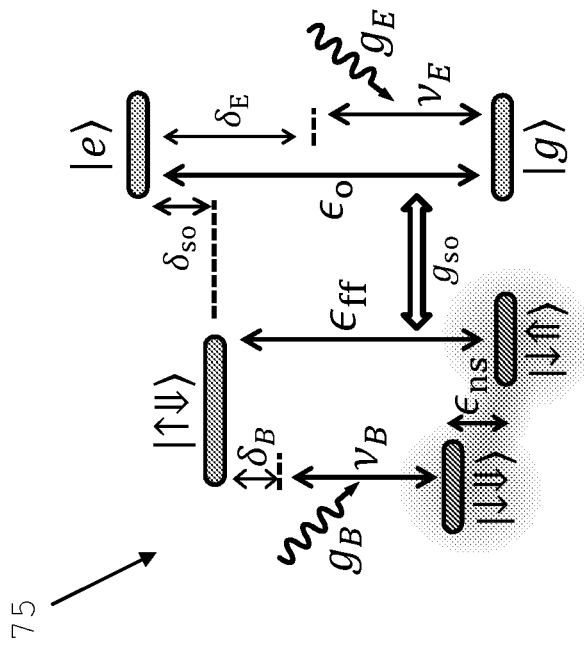
FIG. 7 is a simplified (a) and complete (b) energy level diagram of a nuclear-spin qubit driven using AC electric and magnetic fields, with corresponding spatial schematic view (c)

Referring now to FIG. 7 there is shown a simple schematic energy level diagram 70 of a nuclear-spin qubit driven using AC electric and magnetic fields. With the electron spin down, the nuclear spin transition frequency is $$\varepsilon_{ns}(A) = \frac{A(E_z)}{2} + \frac{\sqrt{(\gamma_+ B_0)^2 + [A(E_z)]^2} - \gamma_- B_0}{2} \tag{15}$$

Figure 7C:
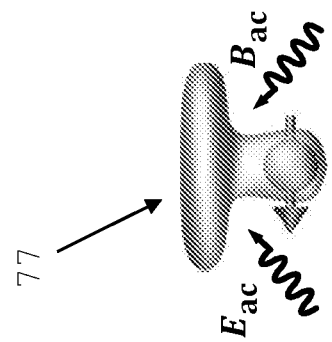

Rather than using a simple AC magnetic field drive with frequency equal to $\varepsilon_{ns}$, the nuclear-spin qubit can be driven using a combination of AC electric and magnetic fields at much higher frequencies. The spatial representation 77 of such a drive is shown in FIG. 7(c). The magnetic drive Hamiltonian is:

$$\mathcal{H}_{ESR} = B_{ac}\cos(2\pi\nu_B t)(\gamma_e S_x - \gamma_n I_x) \tag{16}$$

The total Hamiltonian describing nuclear spin drive by AC electric and magnetic fields at microwave frequencies is:

$$\mathcal{H}_{drive}^{nuc} = \mathcal{H}_{B_0} + \mathcal{H}_A^{orb} + \mathcal{H}_{orb} + \mathcal{H}_E + \mathcal{H}_{ESR} \tag{17}$$

With the nuclear spin down, the electron spin resonance (ESR) frequency is $\epsilon_{ff}-\epsilon_{ns}$. In the drive process, excitation of the electron spin states is prevented by detuning the drives from the transition frequencies by an amount much larger than the coupling rates, i.e., $\delta_E-\delta_{so}\gg g_E^{ff}$ (recall FIG. 4(c)) and $\delta_B\gg g_B$. As before, electron orbital state is prevented if $g_{so}\ll\delta_{so}$ and $g_E\ll\delta_E$, where $\delta_B=\epsilon_{ff}-\epsilon_{ns}-\nu_B$. A more complete energy level diagram 75 is shown, for reference, in FIG. 7(b).

Under these conditions, the nuclear spin is coupled to the electric drive at a rate, to second order:

$$g_E^{ns} = \frac{g_B g_E^{ff}}{2}\left(\frac{1}{\delta_B} + \frac{1}{\delta_E - \delta_{so}}\right) \tag{18}$$

Figure 7A:
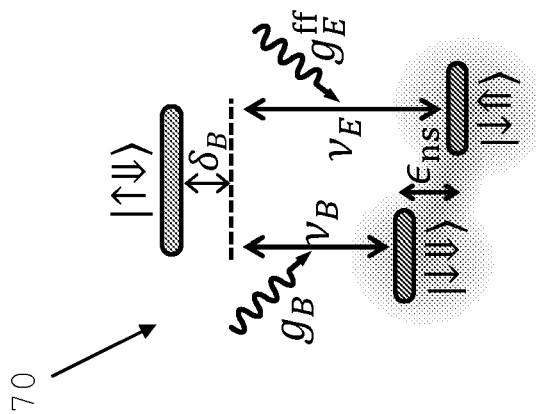

Resonant Raman drive occurs when $\delta_B=\delta_E-\delta_{so}=\delta$ (FIG. 7(a)). A schematic spatial visualization of such a Raman process is shown in FIG. 7(c). For example given earlier of a d=15 nm deep $^{31}$P donor, driven by $E_{ac}$=32 V/m at a rate $g_E^{ff}$=2.9 MHz, avoiding excitation of the electron spin requires $\delta_E-\delta_{so}$=29 MHz. Choosing $g_B=\delta_B/10$=2.9 MHz ($B_{ac}$=0.4 mT), the nuclear spin is driven at a Rabi frequency of $2g_E^{ns}$=0.6 MHz, with 1-qubit operations taking only 0.4 μs. This is two orders of magnitude faster than the typical Rabi frequencies obtained with standard (nuclear magnetic resonance) magnetic drive at radiofrequency.

Referring now to FIG. 8, there is shown a plot 80 of the nuclear spin qubit transition frequency as a function of the applied electric field, when subject to an AC magnetic drive, together with the corresponding energy level diagram 85. Without the AC drive, the bare nuclear spin transition frequency depends roughly linearly on $A(E_z)$ (Eq. 15), which varies strongly with $E_z$ around the ionization point (dashed line in plot 80 in FIG. 8(a)). However, the nuclear spin can also be made highly insensitive to electric noise around the ionization point. This is achieved by adding the AC magnetic field, close to the electron spin transition frequency. This magnetic drive AC-Stark shifts $\epsilon_{ns}$ by an amount dependent on $E_z$, $$\epsilon_{ns}(A, D_{drive}) = \epsilon_{ns}(A) - D_{drive}(E_z), \tag{22}$$

$$D_{drive}(E_z) = \sum_{i=1,2,3}\frac{\delta_i}{2}\left(\sqrt{1+\left(\frac{2g_i}{\delta_i}\right)^2}-1\right), \tag{22a}$$

$$g_1 = \alpha g_B, g_2 = \beta g_B, g_3 = g_B. \tag{22b}$$

The level diagram 85 in FIG. 8(b) defines the detunings $\delta_1$, $\delta_2$ and $\delta_3$.

Most importantly, $\epsilon_{ns}(E_z)$ can be tuned in such a way that in the region 87, close to the ionization point 86, the qubit precession frequency is highly insensitive to electric field noise, again in a similar fashion to atomic clock transitions.

By displacing the electron wavefunction towards the interface, there is a concentration of positive charge at the donor location and negative charge at the interface. This electric dipole, with modulus ed, produces a vertical electric field on the horizontal plane around the donor.

The coupling of two donor spin qubits via dipole-dipole interaction is an important feature of the scalable quantum processor envisaged by the Applicants.

Referring now to FIG. 9 there is shown a flow-diagram 90 with the basic steps used to couple two flip-flop qubits by using this electric dipole. At step 92, a continuous magnetic field applied to the quantum processing elements to separate spin states associated with an electron and a nucleus of two donor atoms in two processing elements. At step 94, an electric signal is applied to each of the conductive electrodes of the two processing elements to displace the electrons and create two electric dipoles associated with the respective processing elements to enable coupling of the quantum states of the two quantum bits associated with the two processing elements.

Figure 10B:
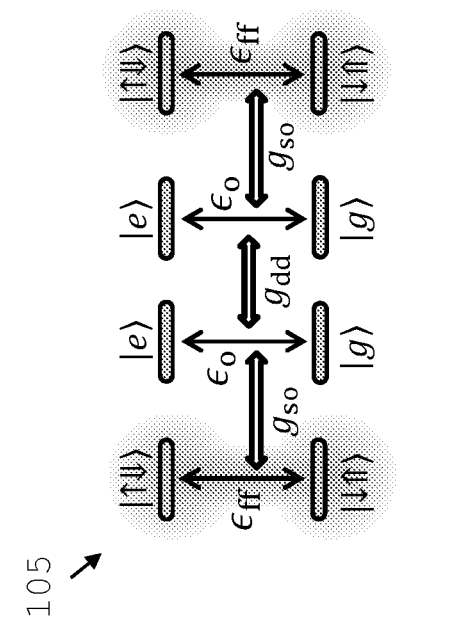
FIG. 10 is a schematic illustration of two processing elements coupling via electric dipole-dipole interaction (a) and an energy level diagram of two 'flip-flop' qubits coupling via electric dipole-dipole interaction (b)
Figure 10A:
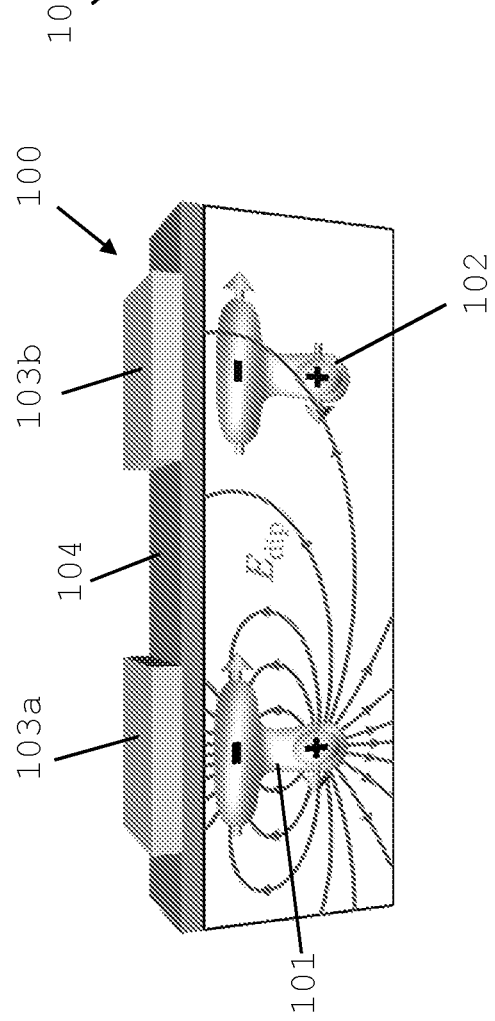

FIG. 10(a) shows a schematic 100 structure with two electric dipoles 101 and 102 for respective processing elements. Schematic 100 also shows electric field lines generated by dipole 101. The dipoles are controlled using electrodes 103a and 103b respectively through dielectric layer 104.

Electrons on the verge of ionization are displaced according to this electric dipole field, which is equivalent to a coupling term between the orbital states of both donors.

The interaction energy between two distant dipoles, $\mu_1$ and $\mu_2$, oriented perpendicularly to their separation, r, is $V_{dip}=\mu_1\mu_2/(4\pi\varepsilon_r\varepsilon_0 r^3)$ where $\varepsilon_0$ is the vacuum permittivity and $\varepsilon_r$ the material's dielectric constant ($\varepsilon_r$=11.7 in silicon). The electric dipole of each donor-interface state is $\mu_i=ed_i(1+\sigma_{z,i})/2$, implying that the dipole-dipole interaction Hamiltonian is:

$$\mathcal{H}_{dip} = g_{dd}(\sigma_{z,1}\sigma_{z,2} + \sigma_{z,1} + \sigma_{z,2}) \quad (23)$$

$$g_{dd} = \frac{1}{16\pi\varepsilon_0\varepsilon_r h}\frac{ed_1 ed_2}{r^3} \quad (24)$$

Since the flip-flop spin qubit is coupled to the electron orbital position, a natural way of coupling two distant donor spins is via this dipole-dipole interaction.

The coupling technique exploits the electric dipole that naturally arises when a donor-electron wave-function is biased to the ionization point, due to the fact that a negative charge has been partly displaced away from the positive $^{31}$P nucleus. The electric field produced by this induced dipole can, in turn, introduce a coupling term in a nearby donor which is also biased at the ionization point.

This electric dipole-dipole interaction is therefore equivalent to a transverse coupling term between the charge qubits plus a small shift in the equilibrium orbital position of both electrons. Most importantly, since each flip-flop qubit is transversely coupled to their electron position the electric dipole-dipole interaction provides a natural way to couple two distant qubits.

FIG. 10(b) shows an energy level diagram 105 of two 'flip-flop' qubits coupling via electric dipole-dipole interaction. The flip-flop qubits are coupled while keeping the orbital levels in their ground state. The Hamiltonian of the system reads:

$$\mathcal{H}_{flip-dip} = \mathcal{H}_{dip-dip} + \Sigma_{i=1,2} \mathcal{H}_{B_0}{}^i + \mathcal{H}_A{}^{orb,i} + \mathcal{H}_{orb}{}^i \quad (25)$$

Fastest coupling rates are achieved if all levels are in resonance, $\epsilon_{ff}=\epsilon_o$. If $\epsilon_o \gg g_{dd} \gg g_{so}$, electron orbital excitation is minimized and the flip-flop qubits are coupled at a rate, to second order:

$$g_{2q}{}^{ff}=(g_{so})^2/g_{dd} \quad (26)$$

For a pair of $^{31}$P donors with $d_1=d_2=15$ nm, $g_{dd}\approx 10\ g_{so}$ requires r=180 nm. At this distance, $g_{2q}$=3 MHz and therefore a $\sqrt{iSWAP}$ gate takes only 40 ns.

Electric field noise during dipole-dipole coupling may affect the qubit states in the presence of electric field noise. If the noise is such to affect the qubit states, the qubits can be operated at bias points that render the qubit precession frequency highly robust against noise.

Referring now to FIG. 11 there is shown a flow-diagram 110 with the basic steps used to couple two nuclear-spin qubits via electric dipole-dipole interaction. At step 112, a continuous magnetic field applied to the quantum processing elements to separate spin states associated with an electron and a nucleus of two donor atoms in the two processing elements. At step 114, an oscillating magnetic field is applied in a direction perpendicular to the continuous magnetic field. The field oscillates at a frequency close to a Zeeman frequency of the electron to each of the processing elements. At step 116, an electric signal is applied to each of the conductive electrodes to displace the electrons and create two electric dipoles associated with the respective processing elements and enable coupling of the quantum states of the two nuclear-spin qubits associated with the two processing elements.

Figure 12:
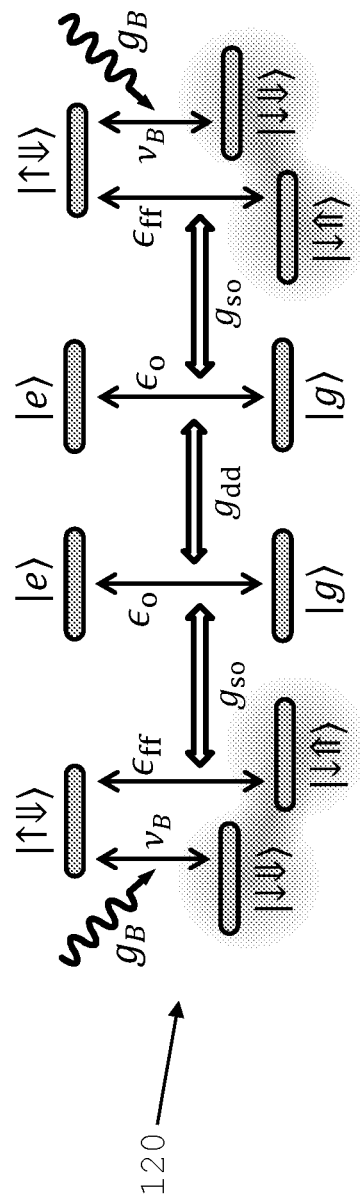
FIG. 12 is an energy level diagram of two nuclear-spin qubits coupling via electric dipole-dipole interaction.

FIG. 12 is an energy level diagram 120 of two nuclear-spin qubits coupling via electric dipole-dipole interaction.

The oscillating magnetic field with frequency close to the electron Zeeman frequency couples the spin states $|\downarrow\Downarrow\rangle$ and $|\uparrow\Downarrow\rangle$. The Hamiltonian representing the system dynamics reads:

$$\mathcal{H}_{nuc-nuc} = \mathcal{H}_{dip-dip} + \Sigma_{i=1,2}\mathcal{H}_{orb}{}^i + \mathcal{H}_A{}^{orb,i} + \mathcal{H}_{B_0}{}^i + \mathcal{H}_{ESR}{}^i \quad (27)$$

The driving frequency $\nu_B$ can be selected to be in resonance with the ESR transition and the flip-flop transition to be in resonance with the tunnel coupling, $\epsilon_o = \epsilon_{ff} = \nu_B + \epsilon_{ns}$. Under the condition $g_B \ll g_{2q}{}^{ff}$, the electron spins and orbital states are minimally excited and the SWAP rate between distant nuclear spins is, to second order:

$$g_{2q}^{ns} = \left(\frac{g_B}{g_{so}}\right)^2 g_{dd} \quad (28)$$

For the two $^{31}$P donors at $d_1=d_2=15$ nm and z=180 nm apart, $g_{2q}{}^{ff}$=3 MHz imposes the maximum AC magnetic field to be $B_{ac}$=40 μT. This yields $g_{2q}{}^{ns}$=0.3 MHz and therefore a nuclear spin $\sqrt{iSWAP}$ gate time of 4 μs.

Nuclear spin SWAP takes place without excitation of the electron spin, and therefore there is no obvious reason to prevent flip-flop to orbital transitions by imposing $g_{dd} \gg g_{so}$. There is one particular regime, in which $g_{so}=g_{dd}$, where nuclear spin SWAP is faster and moreover electron orbital and spin excitation is still prevented if $g_B \ll (g_{so})^2/g_{dd}$. This sets r=385 nm and $B_{ac}$=0.4 mT ($g_B=g_{so}/10$), then $g_{2q}{}^{ns}$=0.3 MHz. This yields a nuclear spin $\sqrt{iSWAP}$ gate time of 0.4 μs. This is a remarkable advantage over previously proposed architectures for which $\sqrt{iSWAP}$ gates between two $^{31}$P nuclear spins r=15 nm apart takes 3 μs.

FIG. 13 shows a schematic view of a structure 130 for coupling qubits (132 and 134) via a photonic link 136 and the energy level diagram 131 for flip-flop qubit coupling to photons via off-resonant charge states.

In order to couple a spin-qubit to a flying photon, the latter has to be confined to a spatial region, inside of which the qubit is located, for a time long enough as for the interaction to happen. Even though 3D cavities have the longest photon lifetimes, coplanar waveguide resonators (CPWRs) confine the photons into smaller volumes, increasing the magnitude of the vacuum field.

Distant donors may be subject to the vacuum electric field $E_{vac}$ of a shared microwave resonator, by placing them at regions where such a field is high, as for example at electric field antinodes, close to the center-line of ground-plane edges.

Figures 13A, 13B:
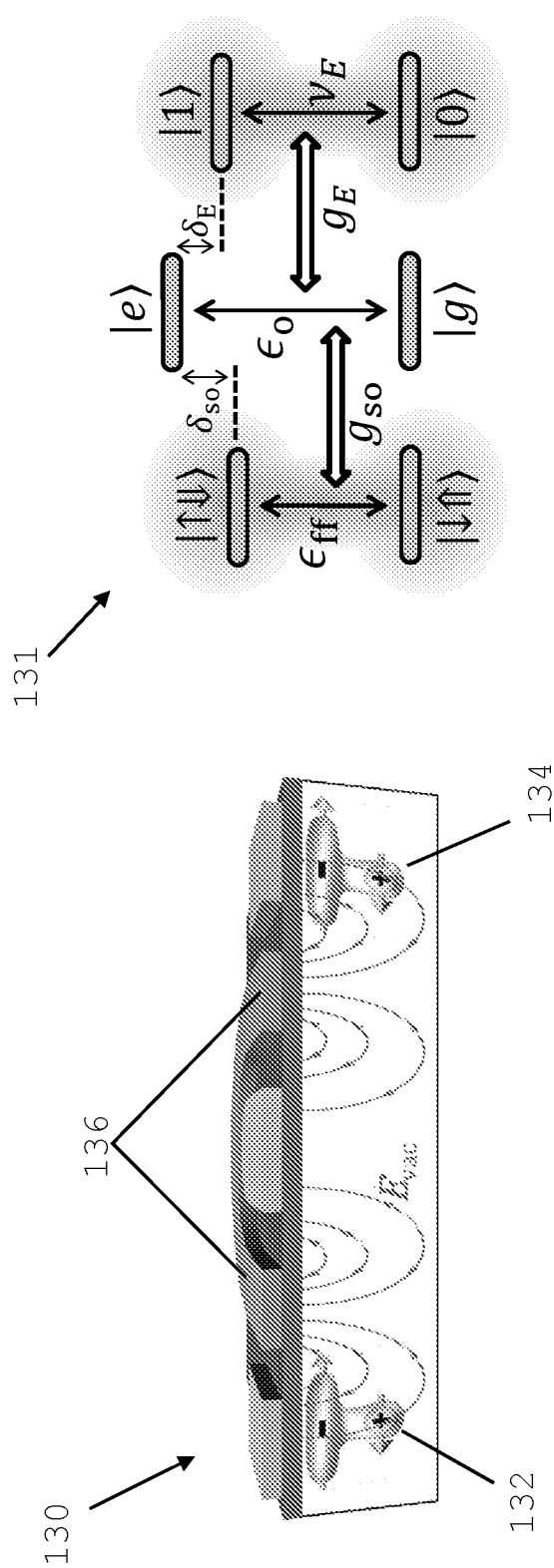
FIG. 13 shows a possible structure for coupling two electron-nuclear spin pairs via a common shared resonator mode (a) and an energy level diagram of a 'flip-flop' qubit coupled to a photon in a resonator (b)

A strong vacuum field, on the order of a few tens of V/m, can be obtained by using planar transmission-line superconducting resonators operating at ≈10 GHz, where the gap between the center-line and the ground planes is shrunk to ~$10^{-7}$ m in the area where the donors are located. The resonator can then be used as a quantum bus to couple two spin qubits separated by as far as 1 cm, as shown in FIG. 13(a). The distance is given by the mode wavelength.

FIG. 13(b) is an energy level diagram 130 of a 'flip-flop' qubit coupled to an electromagnetic field mode which is confined into a spatial region in proximity of the processing element. The electromagnetic field modes may be quantized to comprise one or more photons. In diagram 130 the flip-flop qubit is coupled to a single microwave photon. The interaction of the quantized electromagnetic field modes and the electron may be used to enable coupling of the one or more photons to the quantum state of the quantum bit.

Each resonator mode may contain a limitless number of photons. However, at low enough temperatures, $k_B T \ll h\nu_E$ ($\nu_E$ is the fundamental mode frequency), and without driving sources, the resonator is nearly in its ground state and contains no photons, having a vacuum energy of $h\nu_E/2$. The resonator fundamental mode has then an energy that scales linearly with the number of photons according to the Hamiltonian:

$$\mathcal{H}_{ph} = h\nu_E(\alpha^\dagger \alpha + \tfrac{1}{2}), \tag{29}$$

where $\alpha^\dagger$ and $\alpha$ are the photon creation and annihilation operators, respectively. The vacuum energy is due to an oscillating vacuum voltage with amplitude $V_{vac} = 2\nu_E \sqrt{hZ_0}$, where $Z_0$ is the line impedance. At $\nu_E = 10$ Ghz and $Z_0 = 50\Omega$, $V_{vac} \approx 4$ μV. Therefore, a donor placed under the resonator central line will experience a vertical electric vacuum field. The amplitude of such a field depends on the donor depth and the lateral dimensions of the waveguide, which can reach few tens of nanometers if fabricated using electron beam lithography. Vacuum fields of many tens of V/m are expected. Here we assume $E_{vac} = 32$ V/m, consistent with optimum values specified before.

This vacuum field displaces the electron wavefunction according to the orbital-photon coupling Hamiltonian:

$$\mathcal{H}_{orb-ph} = \frac{eE_{vac}d(a^\dagger + a)\sigma_z}{4h}, \tag{30}$$

Including electron and nuclear spins, the Hamiltonian describing the donor-resonator coupled system, in the absence of drive, reads:

$$\mathcal{H}_{flip-ph} = \mathcal{H}_{B_0} + \mathcal{H}_A^{orb} + \mathcal{H}_{orb} + \mathcal{H}_{orb-ph} + \mathcal{H}_{ph} \tag{31}$$

Excitation of the electron orbital state is prevented if $\delta_{so} \gg g_{so}$ and $\delta_E \gg g_E$, for which an effective flip-flop-photon coupling via virtual orbital excitation is achieved at a rate, to second order:

$$g_{flip-ph} = \frac{g_{so}g_E}{2}\left(\frac{1}{\delta_E} + \frac{1}{\delta_{so}}\right) \tag{32}$$

Following the same arguments discussed above, detunings of $\delta_E \approx \delta_{so} \approx 290$ MHz yield a flip-flop-photon coupling rate of $g_{flip-ph} \approx 3$ MHz, for a $^{31}$P donor d=15 nm deep. This is three orders of magnitude faster than the electron-spin coupling rate to a resonator via its magnetic vacuum field. The obtained rate is comparable to the coupling strength obtained by using strong magnetic field gradients but without the need to integrate magnetic materials within a superconducting circuit.

Coupling spin qubits to single microwave photons provides a natural way to transfer quantum information over long distances.

To avoid losses from photon decay, the qubits should be detuned from the resonator by an amount much greater than the qubit-photon coupling rates.

This means $\delta_E^{ff} \gg g_{flip-ph}$, where $\delta_E^{ff} = \nu_E - \epsilon_{ff} = \delta_{so} - \delta_E$. Two qubits are then coupled via a second-order process at a rate:

$$g_{2q}^{ff} = (g_{flip-ph})^2/\delta_E^{ff} \tag{33}$$

For the previous $^{31}$P donor example, assuming $\delta_E^{ff} = 10 g_{flip-ph}$ yields an effective 2-qubit coupling $g_{2q}^{ff} \approx 0.3$ MHz, with a √iSWAP gate that taking only 0.4 μs. This is an outstanding result considering that the separation of the qubits can potentially reach several millimeters.

Moreover, in the dispersive regime ($\delta_{so} - \delta_E \gg g_{flip-ph}$), qubits can be non-destructively read-out via the resonator.

The resonance frequency of the CPW is slightly shifted by an amount that depends on the spin state, $$\nu_E \rightarrow \nu_E \pm \frac{(g_{flip-ph})^2}{\delta_{so} - \delta_E}.$$

This shift reaches 250 kHz for the flip-flop qubit, and can be easily detected for resonator Q-factors on the order of $10^3$.

Figure 14:
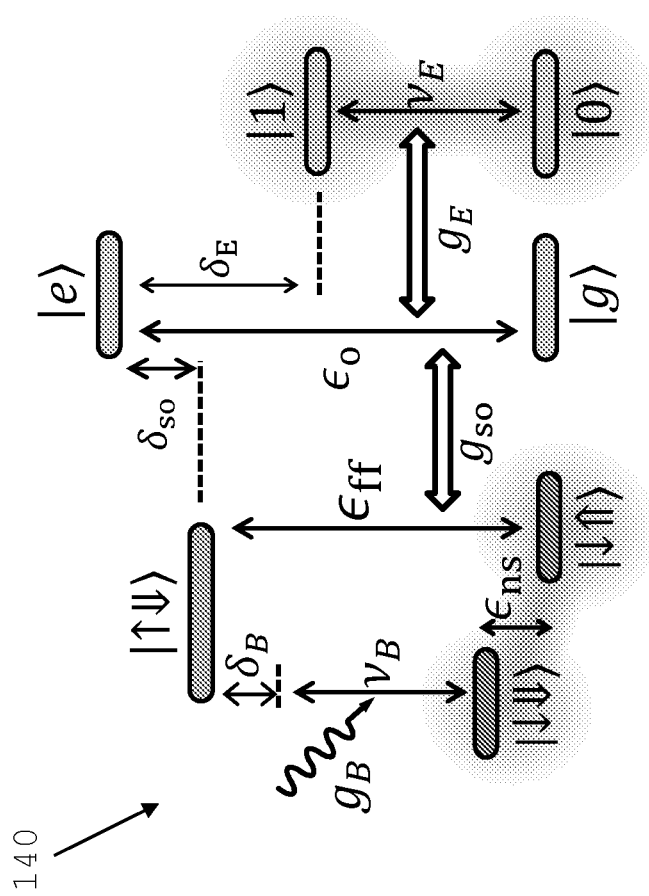
FIG. 14 is an energy level diagram of a nuclear-spin qubit coupled to a photon in a resonator through the addition of an AC magnetic drive.

FIG. 14 is an energy level diagram 140 of a nuclear-spin qubit coupled to a photon in a resonator through the addition of an AC magnetic drive.

The coupling between a flip-flop qubit to a single microwave photon provides a way of coupling the latter to single nuclear spins, by adding an ESR field under conditions that prevent electron spin excitation. This is represented by the nuclear spin-photon coupling Hamiltonian:

$$\mathcal{H}_{nuc-ph} = \mathcal{H}_{B_0} + \mathcal{H}_A^{orb} + \mathcal{H}_{orb} + \mathcal{H}_{orb-ph} + \mathcal{H}_{ph} + \mathcal{H}_{ESR} \tag{34}$$

The electron spin state could be minimally excited if $g_B \ll \delta_B$, for the ESR transition, and $g_{flip-ph} \ll \delta_E - \delta_{so}$ for the flip-flop transition. Excitation of the electron orbital state is prevented if $g_{so} \ll \delta_{so}$ and $g_E \ll \delta_E$. Under these conditions, effective nuclear spin-photon coupling via virtual electron spin and orbital excitation occurs at a rate, to second order:

$$g_{nuc-ph} = \frac{g_B g_E^{ff}}{2}\left(\frac{1}{\delta_B} + \frac{1}{\delta_E - \delta_{so}}\right) \tag{35}$$

For d=15 nm, $E_{ac} = 32$ V/m, $B_{ac} = 400$ μT) a $g_{nuc-ph} = 0.3$ MHz is obtained. This allows for √iSWAP operations between distant $^{31}$P nuclei to be performed within only 4 μs.

In some embodiments, read-out can be performed in the flip-flop qubits subspace, without the addition of an AC magnetic field (note that the nuclear qubit state $|\downarrow \Uparrow\rangle$ shift the resonator frequency mode by 250 kHz whereas the state $|\downarrow \Downarrow\rangle$ does not produce any shift).

Referring now to FIG. 15 there is shown a flow-diagram 150 with the basic steps used to couple two flip-flop qubits via intermediate coupling with a microwave resonator quantized electromagnetic field mode. At step 152, a continuous magnetic field is applied to the quantum processing elements to separate spin states associated with an electron and a nucleus of the donor atoms. At step 154, electromagnetic field modes are confined into a spatial region in proximity of the processing elements in a manner such that a quantized electric field is induced in the region between the interface and the donor atom to modulate a hyperfine interaction between the electron and the nucleus of each processing element and couple the quantum state of the two flip-flop quantum bits.

Referring now to FIG. 16 there is shown a flow-diagram 160 with the basic steps used to couple two nuclear-spin qubits via intermediate coupling with a microwave resonator quantized electromagnetic field mode. At step 162, a continuous magnetic field is applied to the quantum processing elements to separate spin states associated with an electron and a nucleus of the donor atoms. At step 164, an oscillating magnetic field in a direction perpendicular to the magnetic field. The field oscillates at a frequency close to a Zeeman frequency of the electron is applied to each of the processing elements. At step 166, electromagnetic field modes are confined into a spatial region in proximity of the processing elements in a manner such that a quantized electric field is induced in the region between the interface and the donor atom to modulate a hyperfine interaction between the electron and the nucleus of each processing element and couple the quantum state of the two nuclear-spin qubits.

FIG. 17(*a*) shows a schematic representation 170 of two qubit gates between the nuclear spins 172 and 174. Arrow 176 can represent either the direct dipole-dipole or the photonic links. FIG. 17(*b*) shows level diagrams 175 for distant two-qubit (charge, 177, flip-flop, 173, or nuclear-spin, 171) coupling via virtual photons 170.

The nuclear spin is coupled to photons through the electric and magnetic dipole moments of the electron, and it precesses at GHz frequencies in the AC magnetic drive rotating frame, $\epsilon_{ns}+\nu_B$. The shared quantum electric field $E_{vac}$ is sufficient to provide long-distance coupling between nuclear spins, even though $B_{ac}$ is a classical drive. Photon creation is suppressed if $\delta_E^{ns} \gg g_E^{ns}$, where $\delta_E^{ns} = \nu_E - (\epsilon_E + \nu_B)$ is the qubit detuning from the resonator, in the magnetic drive rotating frame.

stitute a single electron transistor. The substrate (183*a*, 183*b*) can be an isotopically purified $^{28}$Si crystal, with a thin oxide layer (189*a*, 189*b*) on top. Substrate regions 184*a* and 184*b* may be highly doped with donors to form an electron reservoir. Metallic contacts 186*a* and 186*b* may set the Fermi energy level of those reservoirs. Applying a highly positive voltage to gates 187*a*, 187*b* and 188 generates an electron gas at the interface underneath, which contacts both reservoir regions, in a process analogous to a MOSFET turn on. Lowering the voltage on gates 187*a* and 187*b*, which are disconnected from gate 188 by the dielectric barriers 185*a* and 185*b*, depletes the electron gas under those gates, creating henceforth two tunnel barriers. Conduction then happens via single electrons, in which case structure 181 may constitute a single electron transistor (SET).

Donors are placed, using for example ion implantation, under the metallic gates 188*b*. Each of those gates can be on top of one or a few donors. Gates 188*b* control the electron wavefunction, which can be displaced between donor and interface as described before. Single qubit operations may be performed by applying AC voltages to gates 188*b*. Two qubit operations are done via electric dipole-dipole coupling between nearby qubits, each of them belonging to different qubit units.

Uncertainties in vertical misplacement of each donor translate into uncertainties in the dipole moment ed and tunnel coupling $V_t$, whereas lateral placement uncertainties changes the electric dipole-dipole coupling $g_{dd}$ between neighboring qubits. The optimum conditions for two qubit coupling are not substantially modified if $g_{dd}$ is altered by an order of magnitude. This translates into a tolerance in donor placement of ~8 nm vertically and many tens of nm laterally, below which the computer performance is not substantially affected. These limits are compatible with the uncertainty in donor placement achieved with ion implantation techniques.

Figure 19:
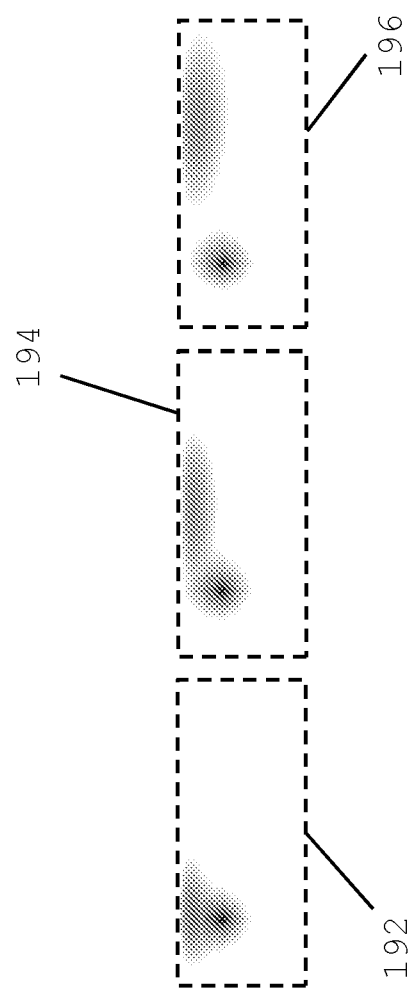
FIG. 19 shows donor-interface electron wavefunctions for different voltages on nearby top gates.

The single donor qubit may be realised using counted ion implantation. In this case, individual extra gates 186*c* and 186*d* may be present at each qubit unit in order to tune the tunnel coupling to the interface. This is shown in detail in FIG. 19, where panels 192, 194 and 196 show electron

TABLE 2

| Qubit | Qubit control | | Photonic link | | Dipole-dipole link | | Electric noise |
|---|---|---|---|---|---|---|---|
| | $\tau_{\pi/2}$ | Power | g (MHz) | $\tau_{\sqrt{iSWAP}}$ | Distance (nm) | $\tau_{\sqrt{iSWAP}}$ | Dephasing |
| Charge | 4 ns | 0.1 pW | $g_E = 30$ | 40 μs | r > 150 | >0.2 ns | 1 MHz |
| Flip-Flop | 40 ns | 0.1 pW | $g^{ff}_E = 3$ | 0.4 μs | r ≈ 180 | 40 ns | 0.1 kHz |
| Nuclear Spin | 400 ns | 1 μW | $g^{ns}_E = 0.3$ | 4 μs | r ≈ 385 | 0.4 μs | 1 kHz |

Table 2 shows the qubit gate time for specified power, figures of merit for each distant coupling scheme, and expected qubit dephasing rates due to electric field fluctuations with rms amplitude $E^{noise}_{z,rms} = 30$ V/m. The optimal inter-qubit distance using dipole-dipole link is slightly larger when effects from image charges at the interface are considered.

FIG. 18(*a*) shows a schematic top view 180 of a possible implementation of a quantum computer consisting of a 2D array of single qubits, with a 200 nm pitch. FIGS. 18(*b*) and 18(*c*) show lateral cuts 181 and 182 corresponding to dashed lines in 180. This processor may be fabricated using standard CMOS industrial techniques. Structure 181 may conwavefunction, shared between donor and interface, inside dashed rectangle in structure 182, for three different voltage combinations applied to gates 186*c* and 186*d* of FIG. 18(*c*). The interface state can be displaced laterally by many tens of nanometers, reducing the overlap between donor and interface wavefunctions, therefore reducing $V_t$ by a few orders of magnitude. Another possibility to increase $V_t$ is to keep an extra even number of electrons at the interface. In this way, the donor electron has a wider wavefunction extension when at the interface, which increases its tunnel coupling to the donor. Also, multiple donors can be implanted per processing element, in which case the most convenient the donor can be individually chosen.

Quantum processing may involve a great sequence of steps. While qubits are not being operated, the information can be 'stored' in the nuclear spin, which may be ionized by using top gates. Ionized nuclear spins are the most coherent of the available qubits used here, and among the most coherent of any quantum system. Loading an electron into the donor-interface system, therefore making it active to quantum operations, may be done by inducing an electron gas under gate 188, and then moving this gas closer to the qubit by changing the voltage on neighbouring gates 186c and/or 186d. In order to better electrically isolate qubits or pairs of qubits when performing operations, an electron gas can circumvent qubits or pairs of qubits and therefore screen is electric interaction with neighbouring stray qubits. Read-out of the qubit spin states may be performed by spin-dependent tunnelling to a reservoir, and detecting such a tunnelling event via a nearby SET.

If the nuclear spin is the one used for operations, the operation of the qubit (for 1- and 2-qubit gates) can be achieved by adiabatically pulling the electron wavefunction to the intermediate state between donor and interface using biasing conductive electrodes 188b.

If, instead, the flip-flop qubit is to be used for operations, the electron has to be pulled to the intermediate orbital position, and then an ESR π-pulse is applied at a frequency $\epsilon_{ff} - \epsilon_{ns}$, which maps the nuclear spin state $\alpha|\downarrow\Uparrow\rangle + \beta|\downarrow\Downarrow\rangle$ into the flip-flop state $\alpha|\downarrow\Uparrow\rangle + \beta|\uparrow\Downarrow\rangle$.

Referring now to FIG. 20, there is shown a schematic representation of an embodiment of quantum processor 200 comprising a plurality of qubits realised and coupled in accordance with the methods described above.

Quantum processor 200 comprises several qubit cells 205 coupled using a CPW resonators 207. Each cell may consist of a bilinear array containing a few qubits. The exploded view 205 of a qubit cell shows the internal architecture of the cell. A bottom view 201 of the cell, that does not show the substrate or interfacing oxide for clarity, shows the donor atoms 202 and a schematic representation of the respective electron wave functions. View 201 also shows all metallic gates that form single electron transistors 204, top-gate electrodes 206, confinement and tunnel coupling gates 208, electron reservoir 209 and CPW resonator 203. In this quantum processor, 2-qubit gates are performed within a cell via electric dipole-dipole interactions, where two qubit belonging to the extremities of different cells can be coupled via a common microwave resonator.

The methods and the quantum processor architectures described herein uses quantum mechanics to perform computation. The processors, for example, may be used for a range of applications and provide enhanced computation performance, these applications include: encryption and decryption of information, advanced chemistry simulation, optimization, machine learning, pattern recognition, anomaly detection, financial analysis and validation amongst others.

The term "comprising" (and its grammatical variations) as used herein are used in the inclusive sense of "having" or "including" and not in the sense of "consisting only of".

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The claims defining the invention are as follows:

1. A method of operation of a quantum processing element, the processing element comprising a semiconductor and a dielectric material forming an interface with the semiconductor, a donor atom embedded in the semiconductor at a distance from the interface, and a conductive electrode disposed on the dielectric material, the method comprising the steps of:
   applying a continuous magnetic field to the quantum processing element to separate spin states associated with an electron and a nucleus of the donor atom;
   applying an oscillating magnetic field which oscillates at a frequency close to a Zeeman frequency of the electron; and
   modulating a hyperfine interaction between the electron and the nucleus in response to applying an oscillating electric field, simultaneously with the oscillating magnetic field, in a region between the interface and the donor atom to control the quantum state of a quantum bit associated with a spin of the nucleus,
   wherein the frequency of the oscillating magnetic field and the frequency of the oscillating electric field differ by about a Zeeman frequency of the spin of the nucleus.

2. The method of claim 1 wherein the frequency of the oscillating electric field is selected to be detuned from the orbital excitation frequency of the electron to prevent orbital excitation of the electron.

3. The method of claim 1 wherein the frequency of the oscillating magnetic field is selected to be detuned from the electron spin excitation frequency to prevent flipping of the electron spin quantum state.

4. The method of claim 1 wherein the oscillating electric signal and oscillating magnetic field induce a transition in the quantum state of the quantum bit.

5. The method of claim 1 wherein the method further comprises the step of applying a biasing electric signal to the electrode to bias the electron in a region of high sensitivity of the hyperfine interaction to the electric field.

6. The method of claim 1 wherein the method further comprises the step of applying a biasing electric signal to the electrode such that approximately half of the electron density resides at the interface, and the other half at the embedded donor atom.

7. The method of claim 1 wherein the method further comprises the step of applying a biasing electric signal to bias the electron in a region in proximity of the interface to minimise an interaction of the quantum state of the quantum bit with an external electromagnetic environment.

8. The method of claim 1 wherein the method further comprises the step of applying a biasing electric signal to bias the electron in a region close to the nucleus to minimise an interaction of the quantum state of the quantum bit with an external electromagnetic environment.

9. The method of claim 1 wherein the method further comprises the step of applying an electric signal to the conductive electrode to displace the electron and create an electric dipole associated with the processing element.

10. The method of claim 9 wherein the method further comprises the step of maintaining the electric dipole for a predetermined period of time to enable coupling with another electric dipole of another processing element via dipole-dipole interaction.

11. The method of claim 1 wherein the method further comprises the steps of confining electromagnetic field modes into a spatial region in proximity of the processing element.

12. The method of claim 11 wherein the electromagnetic field modes are quantized to comprise zero, one or more photons and wherein the interaction of the quantized electromagnetic field modes and the electron enables coupling of the one or more photons to the quantum state of the quantum bit.

13. The method of claim 12 wherein the electromagnetic field modes are confined in a resonator; the resonator comprising a microwave resonating cavity or a coplanar waveguide resonator; and the method further comprises the step of using the quantized electromagnetic modes of the resonator to couple the quantum state of the quantum bit of another processing element to enable long distance quantum bit coupling.

14. A method of coupling quantum states of two processing elements, each of the processing elements comprising a semiconductor and a dielectric material forming an interface with the semiconductor, a donor atom embedded in the semiconductor at a given distance from the interface, and a conductive electrode disposed on the dielectric material, the method comprising the steps of:
applying a continuous magnetic field to the two quantum processing elements to separate spin states associated with an electron and a nucleus of the donor atoms;
applying an oscillating magnetic field to the two quantum processing elements which oscillates at a frequency close to a Zeeman frequency of the electron to each of the processing elements;
modulating a hyperfine interaction between the electron and the nucleus of each processing element in response to applying an oscillating electric field, simultaneously with the oscillating magnetic field, in a region between the interface and the donor atom of each processing element to encode quantum information in the quantum state of each nucleus; and
applying a non-oscillating electric field to each of the conductive electrodes to displace the electrons and create two electric dipoles associated with the respective processing elements to enable coupling of the initialized quantum states of the two nuclei.

15. A method of coupling quantum states of two processing elements, each of the processing elements comprising: a semiconductor and a dielectric material forming an interface with the semiconductor, a donor atom embedded in the semiconductor at a given distance from the interface, and a conductive electrode disposed on the dielectric material, the method comprising the steps of:
applying a continuous magnetic field to the quantum processing elements to separate spin states associated with an electron and a nucleus of the donor atoms; and
confining electromagnetic field modes into a spatial region in proximity of the processing elements in a manner such that a quantized electric field is induced in the region between the interface and the donor atom to modulate a hyperfine interaction between the electron and the nucleus of each processing element and couple the quantum state of a quantum bit associated with a pair of electron-nuclear spin eigenstates of one processing element to a quantum bit associated with a pair of electron-nuclear spin eigenstates of the other processing element.

16. A method of coupling quantum states of two processing elements, each of the processing elements comprising: a semiconductor and a dielectric material forming an interface with the semiconductor, a donor atom embedded in the semiconductor at a given distance from the interface, and a conductive electrode disposed on the dielectric material, the method comprising the steps of:
applying a continuous magnetic field to the quantum processing elements to separate spin states associated with an electron and a nucleus of the donor atoms;
applying an oscillating magnetic field which oscillates at a frequency close to a Zeeman frequency of the electron to each of the processing elements; and
confining electromagnetic field modes into a spatial region in proximity of the processing elements in a manner such that a quantized electric field is induced in the region between the interface and the donor atom to modulate a hyperfine interaction between the electron and the nucleus of each processing element and couple the quantum state of a quantum bit associated with a nuclear spin of one processing element to a quantum bit associated with a nuclear spin of the other processing element,
wherein a frequency of the oscillating magnetic field is related to a resonance frequency of the quantized electromagnetic field by a Zeeman frequency of the spin of the nucleus.

17. A method of operation of a quantum processing element, the processing element comprising a semiconductor and a dielectric material forming an interface with the semiconductor, a donor atom embedded in the semiconductor at a distance from the interface, and a conductive electrode disposed on the dielectric material, the method comprising the steps of:
applying a continuous magnetic field to the quantum processing element to separate spin states associated with an electron and a nucleus of the donor atom; and
applying an oscillating electric field, in a region between the interface and the donor atom to control the quantum state of a quantum bit associated with a pair of electron-nuclear spin eigenstates by modulating a hyperfine interaction between the electron and the nucleus,
wherein the frequency of the oscillating electric field is about the sum of the electron and nucleus gyromagnetic frequencies multiplied by the magnetic field $[(\gamma_n+\gamma_e)B_0]$.

* * * * *